United States Patent [19]

Lanquetin

[11] Patent Number: 5,266,712
[45] Date of Patent: Nov. 30, 1993

[54] PROCESS FOR CRYSTALLIZING THE ORGANIC SUBSTANCES FROM STEROIDAL ORIGIN AND THE THUS OBTAINED COMPOUNDS

[75] Inventor: Michel Lanquetin, La Trinite, France
[73] Assignee: Laboratoire Theramex S.A., Monaco
[21] Appl. No.: 910,284
[22] PCT Filed: Nov. 12, 1991
[86] PCT No.: PCT/FR91/00888
 § 371 Date: Aug. 14, 1992
 § 102(e) Date: Aug. 14, 1992
[87] PCT Pub. No.: WO92/08730
 PCT Pub. Date: May 29, 1992
[30] Foreign Application Priority Data
Nov. 12, 1990 [FR] France .................. 90 13981
[51] Int. Cl.$^5$ .................. C07J 5/00; C07J 7/00
[52] U.S. Cl. .................. 552/574; 552/576; 552/577; 552/597; 552/599; 552/600; 552/607; 552/625; 552/641
[58] Field of Search .............. 552/574, 576, 597, 577, 552/625, 607, 641, 599, 600

[56] References Cited

U.S. PATENT DOCUMENTS

| | | | |
|---|---|---|---|
| 2,096,744 | 10/1937 | Hildebrandt et al. | 552/625 |
| 2,897,216 | 7/1959 | Oliveto et al. | 552/568 |
| 3,007,923 | 11/1961 | Muller et al. | 540/35 |
| 3,053,865 | 9/1962 | Taub et al. | 552/528 |

Primary Examiner—Marianne M. Cintins
Assistant Examiner—Kimberly J. Kestler
Attorney, Agent, or Firm—Bierman and Muserlian

[57] ABSTRACT

A process for crystallizing a pharmaceutically active steroidal product, without mechanical procedure, to obtain a homogeneous granulometric class which may be prepared beforehand, wherein the product which is desired to be crystallized is dissolved in a ternary mixture made of a lipophilic solvent, a hydrophilic solvent and a surface active agent at a temperature close to the boiling point of the mixture of solvents and wherein the mixture of solvents is allowed to revert to a temperature where the crystallization initiates, then, the thus-formed crystals are recovered.

24 Claims, 20 Drawing Sheets

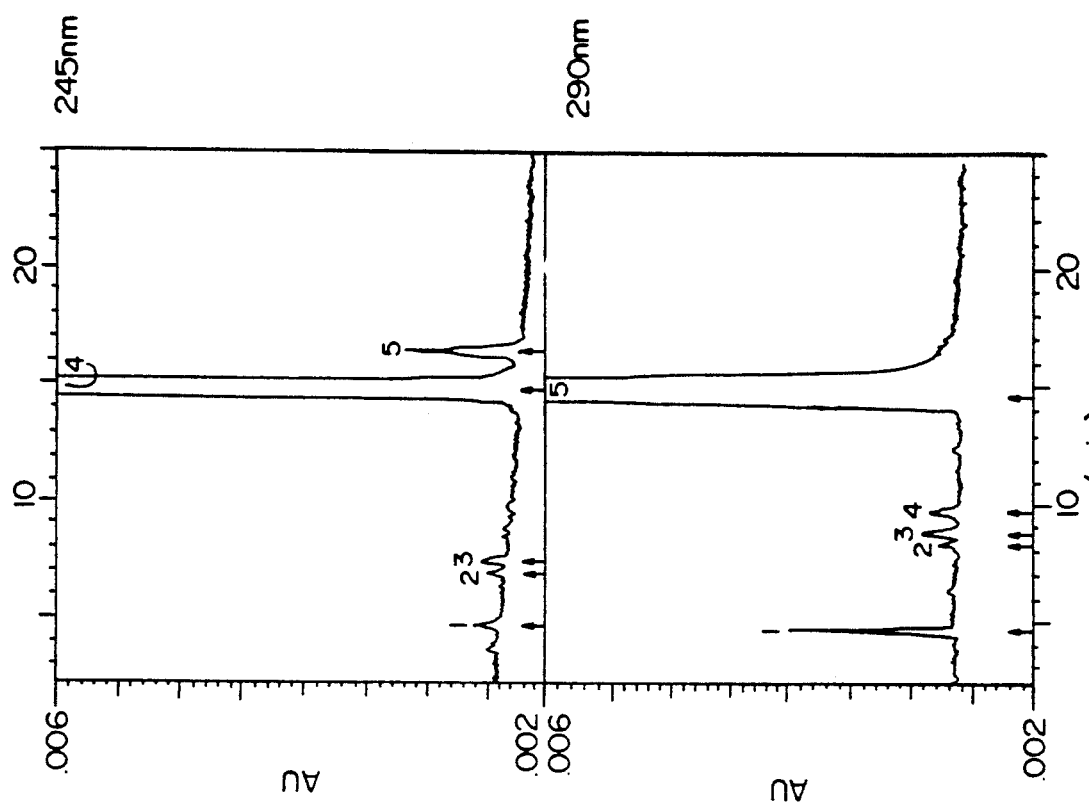
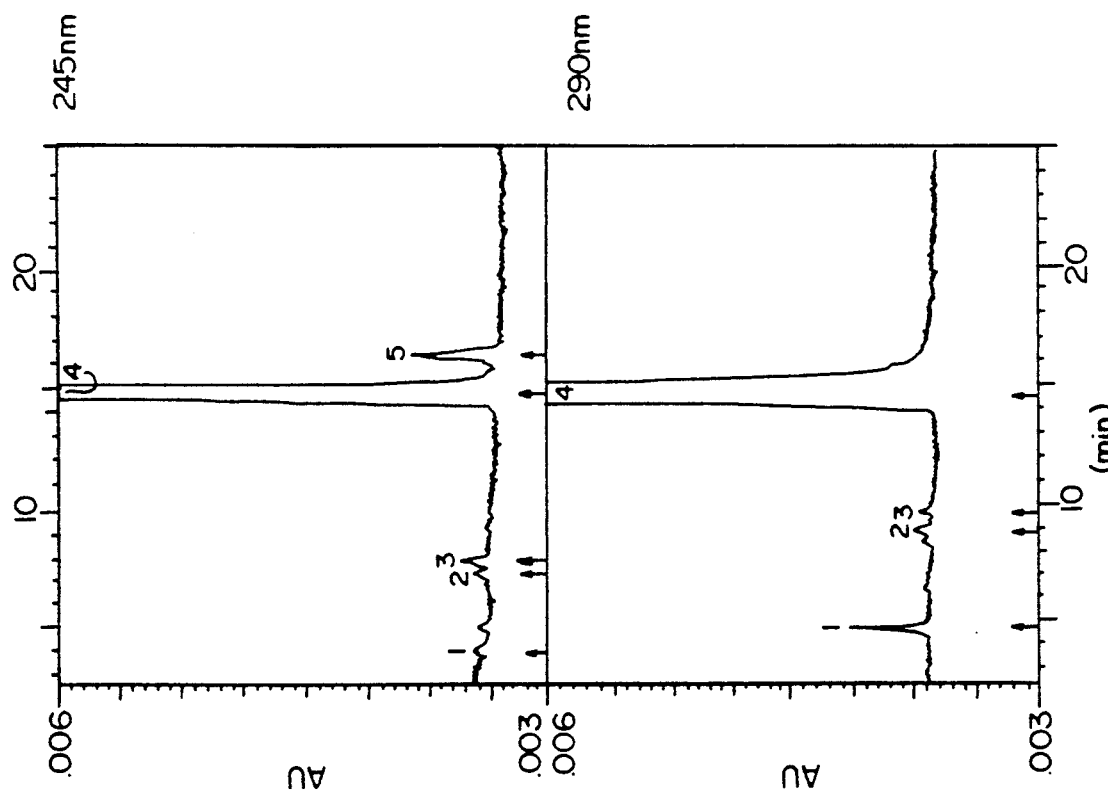

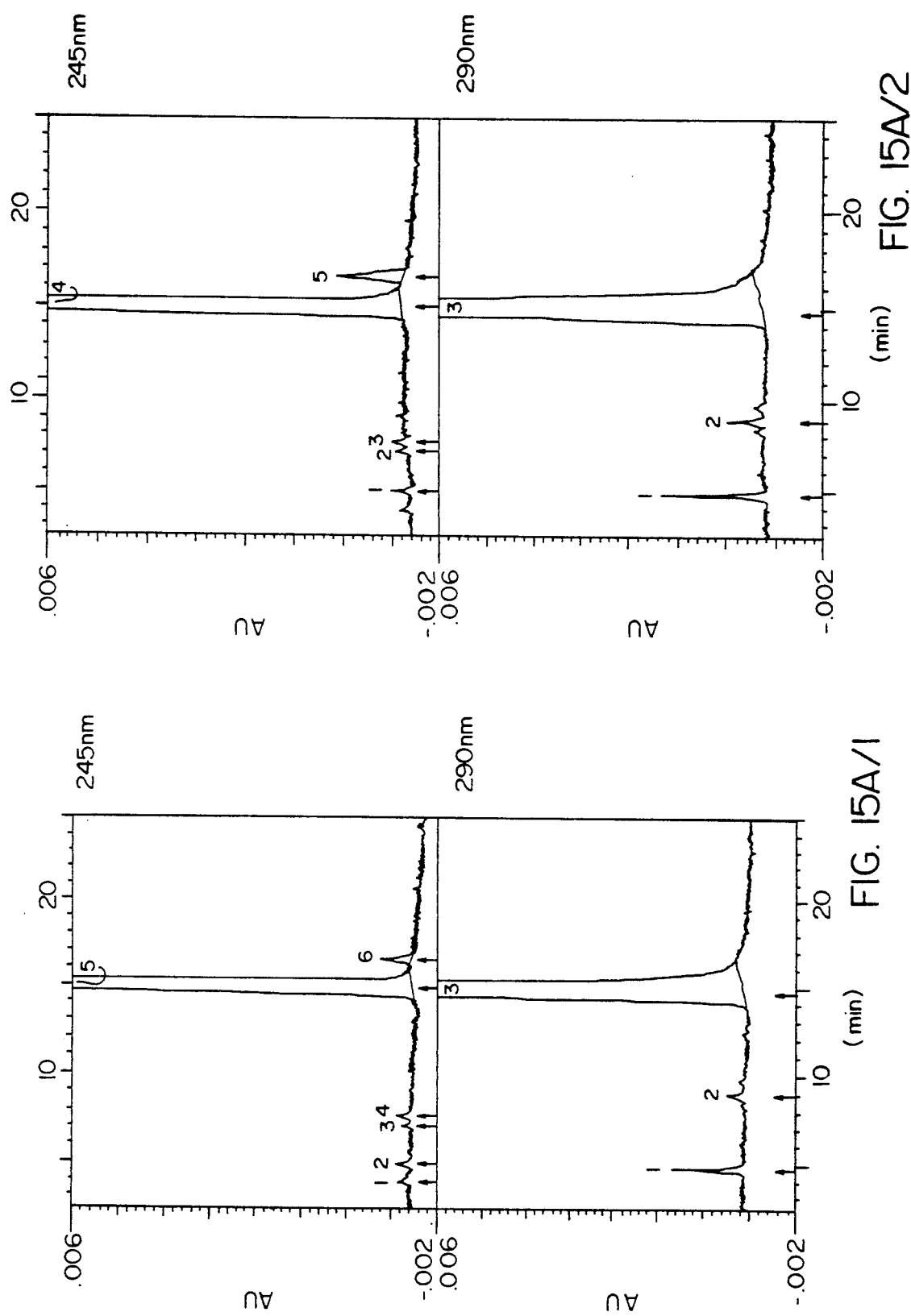

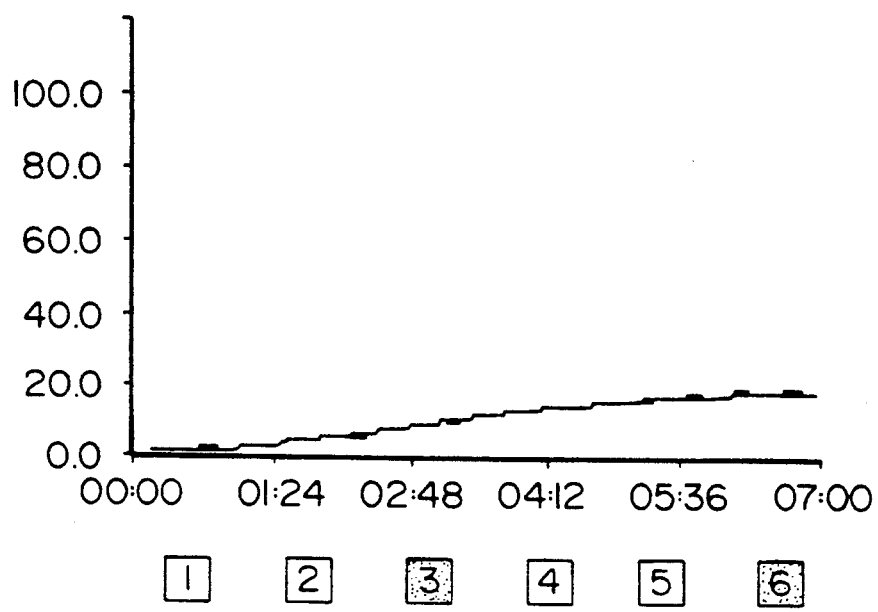
FIG. 21A/1
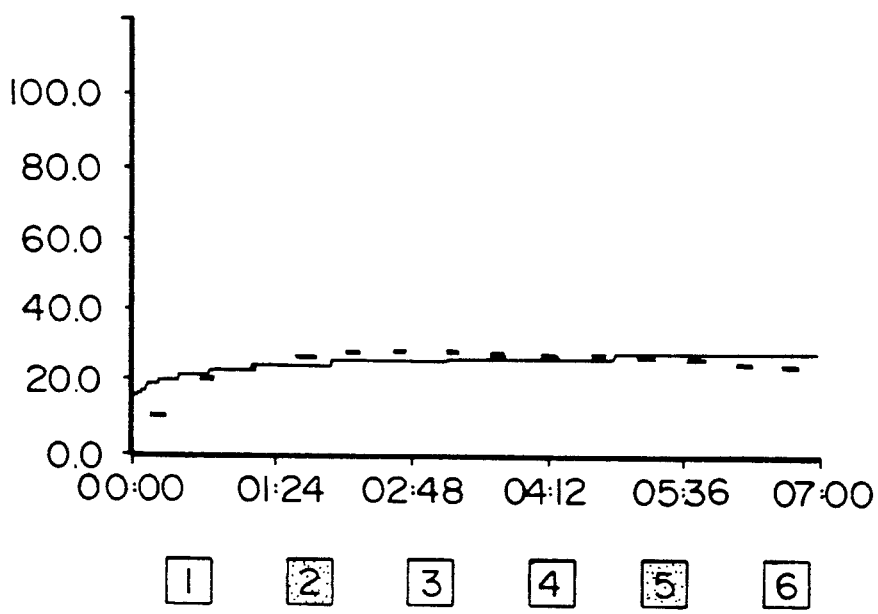
FIG. 21A/2

PROCESS FOR CRYSTALLIZING THE ORGANIC SUBSTANCES FROM STEROIDAL ORIGIN AND THE THUS OBTAINED COMPOUNDS

This invention relates to the field of pharmacotechnology and more particularly it relates to a process for obtaining active ingredients for pharmaceutical use having a determined size of crystals, by means of a crystallization method.

It is in fact known that the size of crystals of a pharmaceutical active ingredient plays an important role when dry or fluid pharmaceutical formulation are realized, to insure a reproducible manufacture of the formulation and hence a constant resorption.

The fact has been frequently cited in the litterature that the variations in the kinetics of dissolution are due either to alterations in the crystalline structure or of the surface properties, of the crystals, or to modifications of the extent of the surface of contact put in action (G. GILLARD Labo. Pharm. Probl. and Techn. 309 (1981) 359–369).

To improve the kinetics of dissolution of the active ingredients of drugs showing a limited solubility, a decrease of the size of the particles are often employed.

This problem is usually solved by the use of a mechanical proceeding such as grinding or micronizing (pounded by jet of air).

A study conducted on various progestatives by Muttenrauch and Cowork (STP Pharma 5(10) 1989, 642–646) has shown that the role played by the size of the crystals on the rate of dissolution was closely linked to the solubility of the organic substances.

It has been often disclosed on a large number of molecules of therapeutic use, that the size of particles and the physico-chemical properties of the active-ingredients resulting from these treatments determine the bioavailability of the pharmaceutical formulation containing them through modifications of the rates and speed of dissolution (cf. FDA paper guidelines, Manuf Control Form ANDA'S (1985). However these methods of pounding are not appropriate to pulverize all active ingredients, some of which have low melting points and become pasty or elastic. Other active ingredients because of their physical properties cannot be micronized (80% <10 µm) and this despite several passages in the pounder. It has been described, namely by Nakagawa and cowork (Chem. Pharm. Bull. 30 (1982) 242) that the specific surface and the crystallinity have a great influence on the chemical stability at the solid state, of the pulverized compound.

The rate of dissolution is also dependant up on the cristallinity of the compound B. A. Hendricken disclosed it in Int. J. of Pharm. 60 243-252 (1990). Other investigators have studied the effects of mechanical treatments, such as grinding, on the physico-chemical properties of various active ingredients contained in the composition of a pharmaceutical formulation for therapeutic purpose. These workers noticed that the active ingredients show some alterations in the physico-chemical properties due to these treatments.

Among them it may be cited:
loss of cristallinity (ascertained using X-rays diffraction)
variations of the specific surface SW which may become double or triple.
a drop in the chemical stability determined through differential thermical analysis of the temperature of decomposition (for some active ingredients it has been noted drops in the melting points of 10° to 15° C.)
a variation in the surface properties which do not make always easy the manufacture of a mixture of powders.

It has more precisely described in the previously-cited Gillard's work that the morphometric, electrical and rheological properties are very significant for the realization of a homogeneous mixture and namely these having a good flowing capacity.

All these changes in the physico-chemical characteristics on various active ingredients have been very precisely described by M. OTSUKA and N. KANENIWA in International J. of Pharmaceutics 62 (1990) 65–73 and in the references cited in this article. Moreover it cannot be forgot ten the influence of the decrease in the size of the particles produced by grinding on the hardness of tablets obtained from these compounds (cf. Y. SAGAWA J. Powder Technol. Jap. 20 (1983) 737–743).

This is why the experimental results from Tawashi (STP Pharma. 6(5) (1990) 299–302) supplied with an illustration of the relation-ship which exists between decrease in the size of the particles and morphological aspects of thus resulting fragments. The result of the mechanism of reduction in the size depending on the utilized means on the measurements of the fragments substantially relate to the evidence of the irregularity of the surfaces of the particles and the relation-ship which exist between the surfaces and physical behaviour of powders during the manufacture of pharmaceutical formulations. Through appearance of the surface, through its influence on the capacity of flowing of the product, constitutes one of the significant factors which have an influence on the qualities of a mixture of powders in order to realize such a pharmaceutical formulation. The effect of the mechanism of reduction in the size also plays an important role on the solubility of the active ingredient.

Other studies have moreover shown that the crystalline form of an active ingredient could still undergo a transformation (crystallisation) or a deformation (such a plastic) during the compression (cf. C. FUHRER, STP Pharma. 6(5) (1990) 294–298).

The grinding may also results in replacing the crystals with agglomerates equivalent to smaller crystals, which do not improve in any manner neither the solubility nor the rate of dissolution of the active ingredient.

Moreover a grinding when mechanical as it is the case with crusher with knifes, may introduce some dirts of the products with metallic particles or with oil.

This invention has then as a subject matter to find a solution which is more satisfactory than the grinding, to obtain a granulometric range of crystals which may be used in the pharmaceutical industry while achieving at will, crystals of a determined size with a quasi constant percentage and which avoids the use of damaging methods for the decrease of the size of particles such as the various publications mentioned and such as the applicant itself, could state it on the experienced active ingredients.

It appeared thus possible to arrive to a solution of this physical problem relating to crystallization and to obtain in this way a homogenous granulometric class of crystals without it would be necessary to have recourse to a grinding or to a sieving and without even modifying the cristalline system of the starting material. This has been ascertained through microscopy and thermal differential analysis (TDA).

The applicant has then searched, to avoid the use of a proceeding of grinding, to exert an influence on the various parameters which control the phenomena of crystallization and namely to modify the constituents of the mass to be crystallized. These procedures have as a goal to exert an influence namely on decisive parameters such as mass transfers and heat transfers. It is known, in fact, that mass transfer is due to a phenomenon of diffusion of the molecules from the liquid mass to the surface of the crystals and that heat transfer is caused by the diffusion of the heat of crystallization (energy of binding released during the period of formation of the crystal) from the surface of crystals to the mass of liquid. A sufficient command of the surimposition of both transfers allows to exert an influence on the growth of the crystals and this to avoid the factor of vicinity of crystals during their formation in concentrated solution.

The latter parameter intervenes for disturbing the regular growth of crystals while causing the formation of agglomerates.

This invention has then as a subject matter a process for crystallizing which through this influence on the parameters of crystallization authorizes without mechanical proceeding, to obtain a homogeneous granulometric range according which the product which is to be crystallized is as a preliminary, dissolved in a ternary mixture made of a lipophilic solvent, a hydrophilic solvent and a surfactant, at a temperature near the boiling point of the mixture of solvents and the resulting solution is cooled to a temperature, where the crystallisation initiates, the thus-formed crystalls which are of the same crystalline system as those at first utilized before they are dissolved in the mixture of solvents but are of the desired size.

Similar processes, except they are in a binary mixture, have already been described for recrystallizing mineral salts such as for example CHIANESE A and cowork. Process Technol. Proc. 89—Vol. 6 (ind. cryst. 87) 261-264 such as sodium perborate, wherein the said authors use a surfactant in water, to recrystallize the said salt, or BLASZCZAK J. and cowork. Kryst. Przem. Krajowe Symp. Mater Konf. 3rd (56 WYAM) 89—95-101 on hydrated Aluminium fluoride.

In the litterature they are also found many publications which study the crystallization to obtain the active ingredients in a well-defined crystalline system, such as for example G.A.J.M.T Sas and cowork which use a process through precipitation to obtain an active ingredient crystallized in the monoclinic system (Eur. Pat. Appl. 389.035) or then to resolve polymorphic forms such as Terfenadin (2 crystalline forms) cf. T. G. Fawcett and al. (U.S. Pat. No. 4,742,175) other scientists have prepared microcrystalls by precipitation in an "anti-solvent"- Schmitt W. achieves this process for microcrystallizing, in dissolving the active ingredient in a hydrosoluble solvent and injecting the aqueous solution into cold carbon dioxide- Microcrystals are thus obtained (PCT Int. Applic. WO 90/03782—CA (1990) 113, 178284 k).

In the process according to this invention, the hydrophilic solvent is selected in such a manner to be miscible or soluble in the lipophilic solvent, to insure a homogeneous solution. Preferably the hydrophilic solvent is an aqueous mixtures of solvents and more particularly water added to a polar solvent and/or a lower alkyl ester.

After numerous searches it appears to be advantageous to select from the family of alkanols (i.e. methanol, ethanol, butanol, isopropanol), of ketons (such as acetone, methylethylketone, and methyl isobutylketone) ethyl acetate, isobutyl acetate inter alia and water, the percentage of which in the binary mixture ranges between 0 and 12%.

The surfactant is preferably a anionic surfactant selected among the polyoxy ethylenic esters of sorbitan and fatty acids having at least 8 carbon atoms, the polyoxy ethylenic ethers of fatty alcohols having at least 8 carbon atoms and the polyoxy ethylenic esters of stearic acid.

The anionic surfactant is selected among those which have an amphiphilic character, but with a predominant hydrophilic character having a HLB>12, such as for example the polyoxy ethylenic esters of sorbitan and a fatty acid such as the TWEENS 20 to 40, the polyoxy ethylenic ethers of fatty alcohols such as the BRIJ 56, 58, 78, 96, 97, 98 and 99, G 3816 and 3820, G 3910 and 3920 or ETHYLAN D 254 to 257, RENEX, CREMOPHOR or of the type PLURONIC (F 68).

The polyoxy ethylenic esters of stearic acid such as the MYRJS 49, 51, 52, 53 and 59 are also suitable because they further improve the dissolution of the active ingredients, they allow to get very-concentrated solutions during the crystallization and to decrease also the, temperature of recrystallization for obtaining the supersaturation of the medium.

As a function of the series of active ingredients to be used, it appears advantageous to utilize a ternary mixture consisting of the previously cited solvents containing from 1 to 12% water and 0,01 to 10% of the surfactant and most preferably from 0.05 to 5%.

This ternary mixture may be produced at once or through several succesive steps in dissolving first the active ingredient in one of the solvents, in adding optionally the surfactant then in making complete the mixture with the other solvent. The volume and the nature of the ternary mixture to be used for the recrystallization, will be selected as a function of the granulometric class to be searched for the studied pharmaceutical form and as a function of the expected yield.

For a definite active ingredient, it will be necessary to establish a ternary diagramm of the mixture to be used and to define the proportion of the solvents which constitute this mixture.

The volume of the ternary mixture depends on the solubility of the active ingredient at reflux temperature in this mixture. A good solubility is required to obtain relatively high concentrations in the mass since this one is an influent factor of the growth of the crystals in the course of cooling.

The presence of water is necessary for some surfactants to insure a good repartition of these ingredients in the liquid mass and thus to promote its incorporation in the network, to form liquid and solid masses in the course of recrystallization and thus to influence the interfacial tension liquid/solid. The effect of vicinity in the course of crystallization may disturb the regular growth of the crystals and lead to groupings having not any clear shape. It is merely the well ordered disposal in the space of the particles composing it, which distinguish the crystals from the amorphous substances wherein the arrangement of the particles is anarchic.

The temperature of heating of the ternary mixture plays an important role. The ternary mixture containing the active ingredient to be crystallized, is lead to a temperature as close as possible from the boiling point of the said mixture in order to insure an high concentration of the substance to be crystallized and in order to be in a position to decrease at most as possible, the temperaure of recrystallization of the said substance.

The size of the thus obtained crystal also varies as a function of the concentration and the ratio lipophilic solvent/hydrophilic solvent. The amount of hydrophilic solvent goes through an optimal value such as for example with the progestative derivatives, between 2 à 5% in the presence of a solvent of the ketonic kind such as methyl ethylketone to obtain a class of crystals the granulometry of which lies between 35 and 70 μm and preferably around 5% to restrict this class between 35 and 55 μm.

With 7.5% of the previously used solvent, the class of crystals raises a new to between 70 and 100 μm. This increase in the content of hydrophilic solvent leads to crystals with higher size. Moreover when operating in a more or less diluted medium, the crystals are caused to be of more or less extended size and to be a function of the nature of the utilized tenside. It appears that the general rule according to which, smaller crystals are obtained if the concentration of the active ingredient is more significant in a medium of crystallization containing only one solvent, is not always verified in this process of crystallization.

The rate of cooling, the temperature of initiation of the recrystallization, the nature of the ternary mixture and the concentration of the active ingredient, are the parameters needed for the selection of a determined granulometry. The cariage of frigories as well as the stirring of the medium will have to be previously defined for each study. The isolation of the active ingredient by filtration is to be carried out at temperatures which may range from +45° to −10° C.

The scale up of this process in the industry for particular compounds, gave rise to some shifts in the granulometric classes. For example for Promestriene at the level of 1 g, crystals of about 50 μm have been obtained, whilst for a batch of 60 kg the same experimental conditions supplied crystals with a granulometry of about 150 μm. Accordingly an adjustment is required when the process has to be adapted to the industrial production.

The active ingredient to be crystallized is preferably a compound having a steroidal structure and particulary a derivative of estrane androstane, pregnane, 19-nor pregnane and cholestane.

Among the derivatives of estrane, it may be cited estradiol, estrone, estriol, 19-nor Testosterone as well as their esters and/or their ethers. A more precise example of derivative of estrane is the 3-propyl ether of the 17-methyl ether of estradiol (Promestriene) or 19-nor Testosterone, Undecanoate.

Among the derivatives of androstane, it may be cited Testosterone, its ethers and ethers in position 17, the substituted Testosterone in position 4,6,7 or 16 such as for exemple 4-chloro Testosterone, 6-methyl Testosterone, 7-methyl Testosterone, the fatty acid esters of Testosterone such as Testosterone cyclopentyl acetate or cyclohexyl propionate, the derivatives of androsta 2-ene substituted in position 17 such as 17-β-acetoxy-17α-ethynyl-5α-androsta-2-ene.

Among the derivatives of pregnane it may be cited progesterone, its enolic ethers, the cyclic or linear enamines, the 17α-hydroxy derivatives thereof, the esters of 17α-hydroxy progesterone, the progesterones substituted in position 1, in position 6, in position 7 or in position 16.

Among the 21-hydroxy pregnenic derivatives, it may be cited the cortisone derivatives such as cortisone, cortisol, prednisone, medrol, dexamethasone, β-methasone or Triamcinolone.

Among the derivatives of 19-nor progesterone it may be cited 17α-hydroxy 19-nor progesterone, its ethers in position 17, its esters in position 17 as well as the substituted 19-nor progesterones such as 6-methyl 17α-hydroxy 19-nor progesterone, its ethers in position 17, its esters in position 17, as well as 6-methyl-3,20-dioxo-17α-hydroxy 19-nor-pregna-4,6-diene and its esters.

Among the cholestanic derivatives it may be cited the biliary acids, cholesterol and its esters, ergosterol, stigmasterol and Calciferol.

The micro-crystalline compounds obtained according to the process of this invention are use ful active ingredients of dry pharmaceutical composition such as uncoated tablets, tablets with slow release, soft gelatine capsules, granulates; or in liquid pharmaceutical compositions such as drinkable suspension or injectible suspensions for intramuscular or intra-articular administration, in vaginal preparations such as suspension, bio-adhesive gels, suppositories or vaginal suppositories.

BRIEF DESCRIPTION OF THE DRAWINGS

FIGS. 1–21 are illustrative of the various test results from the examples. FIG. 1 illustrates the transition enthalpy for solid/liquid transitions of the microcrystallized product. The differential thermic analysis of the raw product, ground product, and microcrystallized product are shown in FIGS. 2–6. FIGS. 7, 11, 12, 15 and 16 show the results of granulometric analysis as determined by a laser granulometer Coulter LS 130. Results of differential thermic analysis of Nomegestrol acetate, before and after grinding, are illustrated by FIGS. 8 and 9, respectively. FIGS. 13 and 14 demonstrate the chromatographic analysis by HPLC of Nomegestrol acetate, before and after grinding, while FIG. 10 illustrates the thermogravimetric analysis of the starting material. FIGS. 17–20 show the granulometric analysis for batches 23, 27, 33 and 35, respectively. (See Example XII) FIG. 21 is a comparison of the dissolution curves.

Figure 1A:
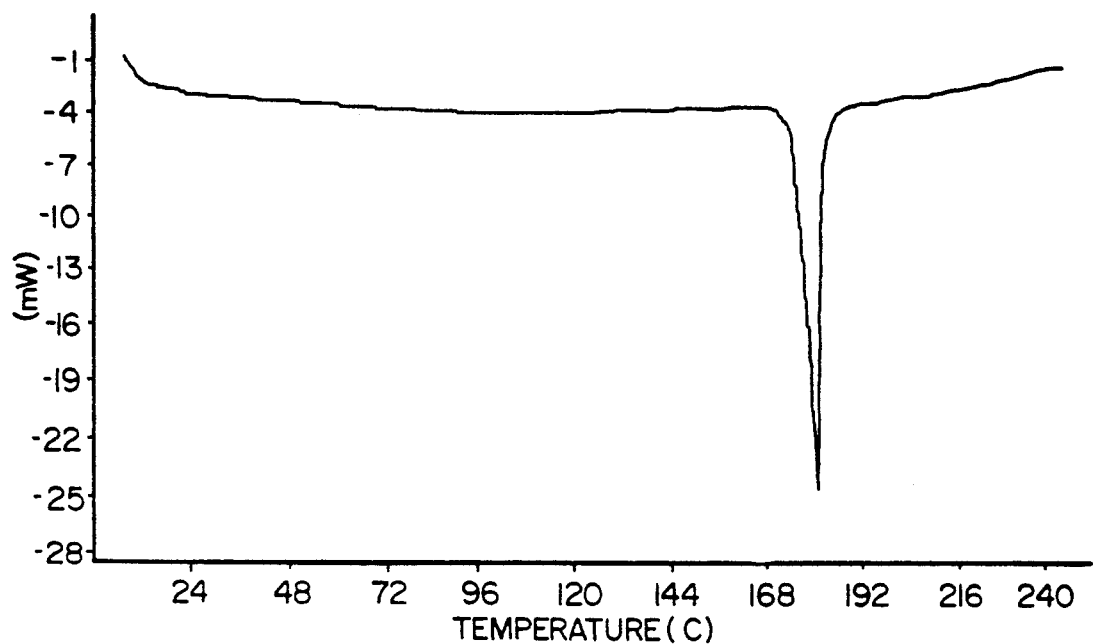

The following examples illustrate this invention without limiting it in any manner. They show the interest of this process in comparison with the conventional grinding.

EXAMPLE I

Microcrystalls of Hydrocortisone 10 g of hydrocortisone are dissolved at reflux temperature in 10 volumes of a solvent mixture formed of:
95.8% methylethylketone
4% water
0.2% Tween 20

It is kept to reflux for 5 to 10 mn under stirring and it has to be sure to it no longer remain any particle suspended. Under stirring, the mass is cooled to −10° C. This temperature is maintained for one hour and the resulting crystals are dried. The crystals are washed with water and further dried under reduced pressure, at a temperature close to 50°–60° C. The thus formed crystals are of 25×30 μm for the biggest ones to 5×10 μm for the smallest ones.
MPk: 221.5°–222° C.

$[\alpha]_D$ (methanol) = +156°±2°

EXAMPLE II

Microcristalls of Dexamethasone Acetate 10 g dexamethasone acetate are dissolved at reflux temperature in 4 vol. of a solvent mixture made of:
89.0% methylethyl ketone
10.5% water
0.5% MIRJ 51

The reflux is kept for 30 mn. The insoluble particles are filtered and the filtrate is cooled to −15° C. This temperature is maintained for 1 hour before drying the crystalline mass. The crystals are washed with water then dried at 60° C. under reduced pressure. The size of the thus formed crystals extends from 80×50 μm for the biggest ones to 8×10 μm for the smallest ones.
MPk = 226°-227°
$[\alpha]_D$ (methanol) = +84°±2°

EXAMPLE III

Microcrystalls of Dexamethasone Acetate 10 g of Dexamethasone acetate are dissolved at reflux temperature into 4 vol. of a solvent made of:
87.6% acetone
12.0% water
0.4% TWEEN 20

Isolation is carried out as described in the preceding example and crystals are obtained the range of which extends from 200×75 μm for the biggest ones to 160×50 μm for the smallest ones.
MPk = 228° C.
$[\alpha]_D$ (methanol) = +86°±2°

EXAMPLE IV

Microcrystalls of Prednisone 10 g prednisone are dissolved in 5 vol. of a solvent mixture made of:
94.8% methylethyl ketone
5.0% water
0.2% TWEEN 20

Isolation of the crystals is performed as described in the foregoing examples (cooling to −10° C.). It is obtained crystals the maximum size of which, is about 55×40 μm and the minimal size of which is 35×24 μm.
MPk = 240°±1° C.
$[\alpha]_D$ (methanol) = +167°±4°

EXAMPLE V

Microcrystalls of Nomegestrol Acetate 10 g Nomegestrol acetate are dissolved at the reflux temperature in 6 Vol. of a solvent mixture made of:
94.9% methanol
5.0% water
0.1% TWEEN 20

The temperature is let to revert very slowly under stirring using external cooling to −5° C. This temperature is maintained for 15 mn. The crystalline mass is separated, dried then washed with water and dried again under reduced pressure.

The thus-formed crystals range from 50×25 μm for the bulkiest ones to 10×10 μm for the smallest ones.

EXAMPLE VI

Microcrystalls of Nomegestrol Acetate

The procedure of example I is followed but using 2 vol. of a ternary solvent mixture made of:

92.4% methylethyl ketone
7.5% water
0.1% TWEEN 20

The microcrystals are recovered, the size of which ranges from 100×100 μm for the bulkiest ones to 65×35 μm for the smallest ones.

EXAMPLES VII

Microcristalls of Nomegestrol Acetate

The same procedure than at example I is used but utilizing 2 vol. of a ternary solvent mixture made of:
94.9% methylethyl ketone
5.0% water
0.1% TWEEN 20

The microcrystals are recovered, the size of which ranges from 55×40 μm for the bulkiest ones to 35×25 μm for the smallest ones.

EXAMPLE VIII

Microcrystals of Nomegestrol Acetate

The same procedure than at example I has been used but using 2 vol. of a ternary solvent mixture formed of:
87.9% methylethyl ketone
12.0% water
0.1% TWEEN 20

The microcrystals are recovered, the size of which ranges from 150×65 for the bulkiest ones to 90×50 μm for the smallest ones.

EXAMPLE IX

Microcrystalls Of Nomegestrol Acetate

The same procedure than at example I is used but utilizing 1,5 vol. of a ternary solvent mixture made of:
94.9% methylethyl ketone
5.0% water
0.1% TWEEN 20

The microcrystals are recovered the size of which ranges from 120×40 μm for the bulkiest ones to 75×50 μm for the smallest ones.

EXAMPLE X

Microcristalls Of Promestriene

The same procedure than at example I is used but dissolving one part of Promestriene in 4 vol. of a ternary solvent mixture made of:
94.9% ethanol at 100%
5.0% water
0.1% TWEEN 20

The crystals are recovered, the size of which ranges from 300×100 μm for the bulkiest ones to 100×50 μm for the smallest ones.

EXAMPLE XI

Microcrystalls Of Promestriene

The same procedure than at the fore going example has been followed in dissolving 30 kg Promestriene in 3 vol. of a ternary solvent mixture made of:

| 94.8% methylethyl ketone | (i.e 85.320 l) |
| 5.0% water | (i.e 4.500 l) |
| 0.2% TWEEN 20 | (i.e 0.180 l) |

The mixture is cooled to −10° C. After 15 mn at this temperaure, the thus-formed crystals are filtered. They were washed with water and dried in a oven at about 35° under reduced pressure. The thus recovered crystals have a size which ranges from 125×100 μm for the bulkiest ones to 80×50 μm for the smallest ones.

The compounds which have been used for these studies (raw compounds, ground compounds and microcrystallised compounds) have been controlled through differential thermic analysis.

Separated studies comparing a raw product and a ground product (Ref. C.114 and C.114B) comparing two ground compounds (C.108B and C.114B) and comparing a raw compound and a microcrystallized product (C.109 and C.109M) have given the following results:

between the tested products from the batches C.108B, C.114B and C.114 in similar experimental conditions in the field of temperatures ranging from 12° to 142° C., these three compounds show through differential thermic analysis with temperature scanning, similar behaviours (see FIGS. 2,3,4,5 and 6).

The melting of these compounds appears to be similar between them, with temperature located in the neighborhood of 64° C. and a melting enthalpy ranging from 72 to 74 joules/g.

The microcrystallized product has a melting temperature of 64.57° C. and melting enthalpy located at 73.2 joules/g, thus very close to that of the other compounds.

EXAMPLE XII

Microcrystalls of Nomegestrol Acetate

Two assays of crystallization have been carried out along the procedure of this invention, starting from 30 kg of Nomegestrol acetate.

The starting material is dissolved in 4 vol. of a ternary solvent made of:
94.9% methanol
5.0% water
0.1% TWEEN 20

The resulting crystalline product is recovered and shows the granulometric range as follows (as determined with a laser granulometer Coulter LS 130):
assay 1: batch 037 MC 2
assay 2: batch 037 MC 3 (see FIG. 7)

For these two assays the results are statistically similar for a definite granulometric range, all the particles of which are inferior to 400 μm.

On the contrary when grinding various industrial batches, it has been stated a large irregularity in the range of the granulometric classes (cf. curves of the batches 23, 27, 33 and 35 in FIGS. 17 to 20).

EXAMPLE XIII

Assays have been performed on larger patches of Nomegestrol acetate using 40, 60 and 90 kg respectively, according to the procedure disclosed in example XII. The results have been as good as the preceding ones.

Figure 16:
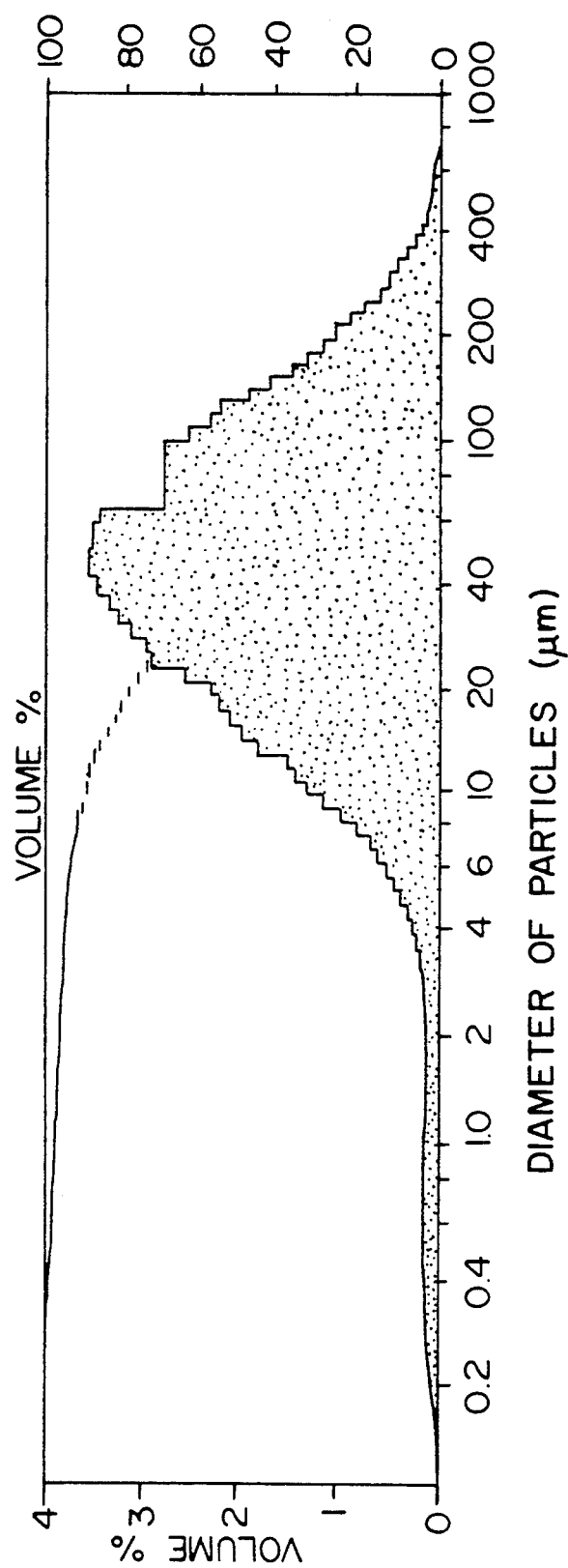
Figure 17A:
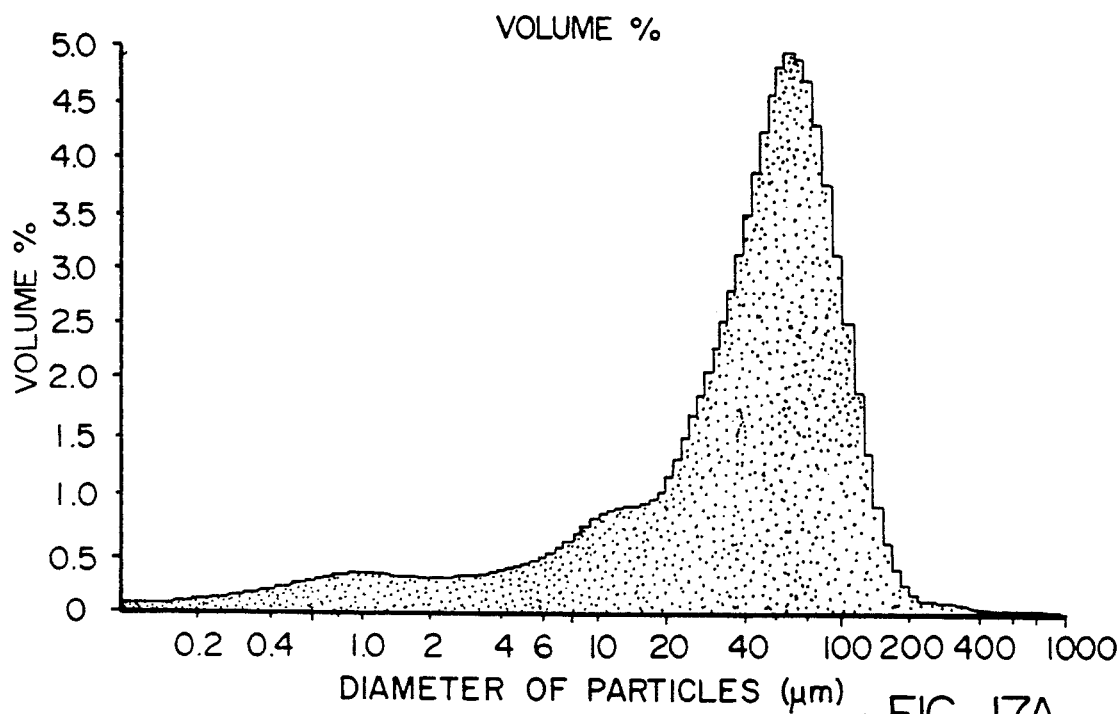
Figure 17B:
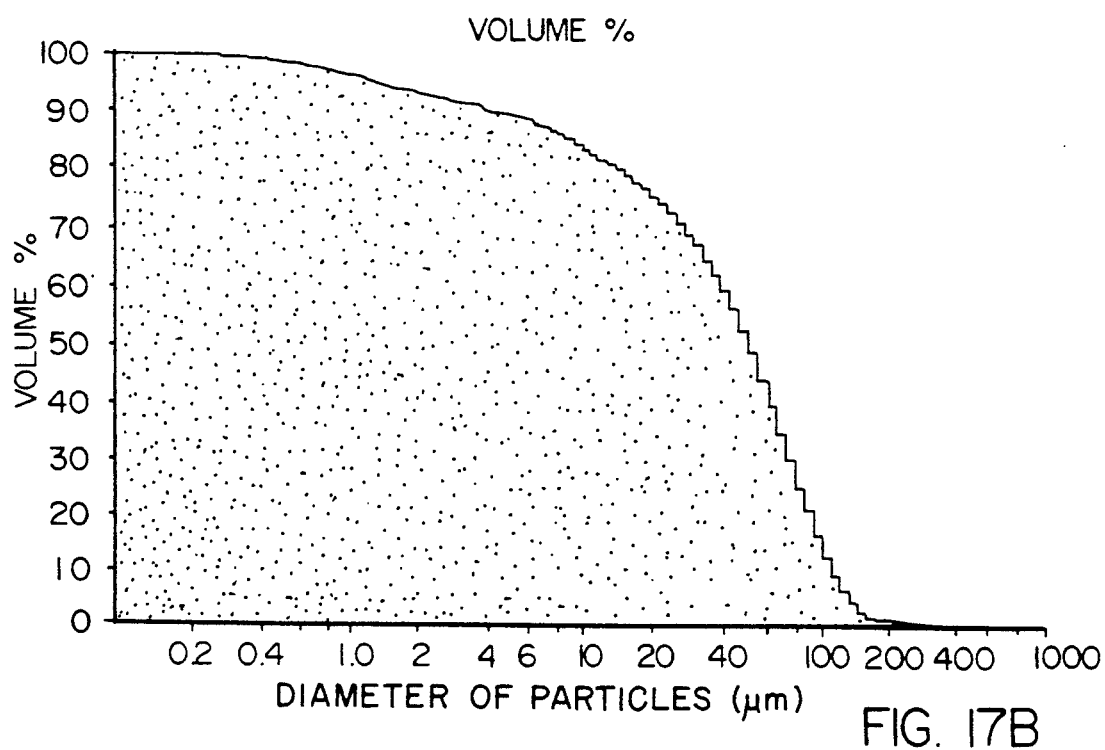
Figure 18A:
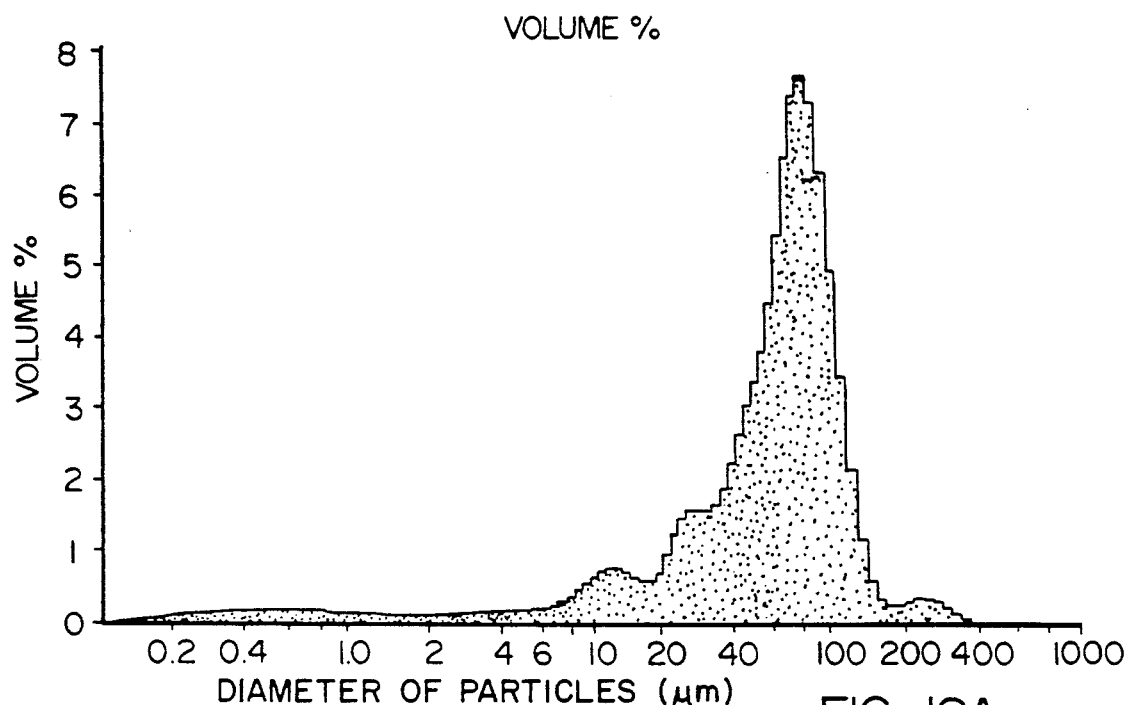
Figure 18B:
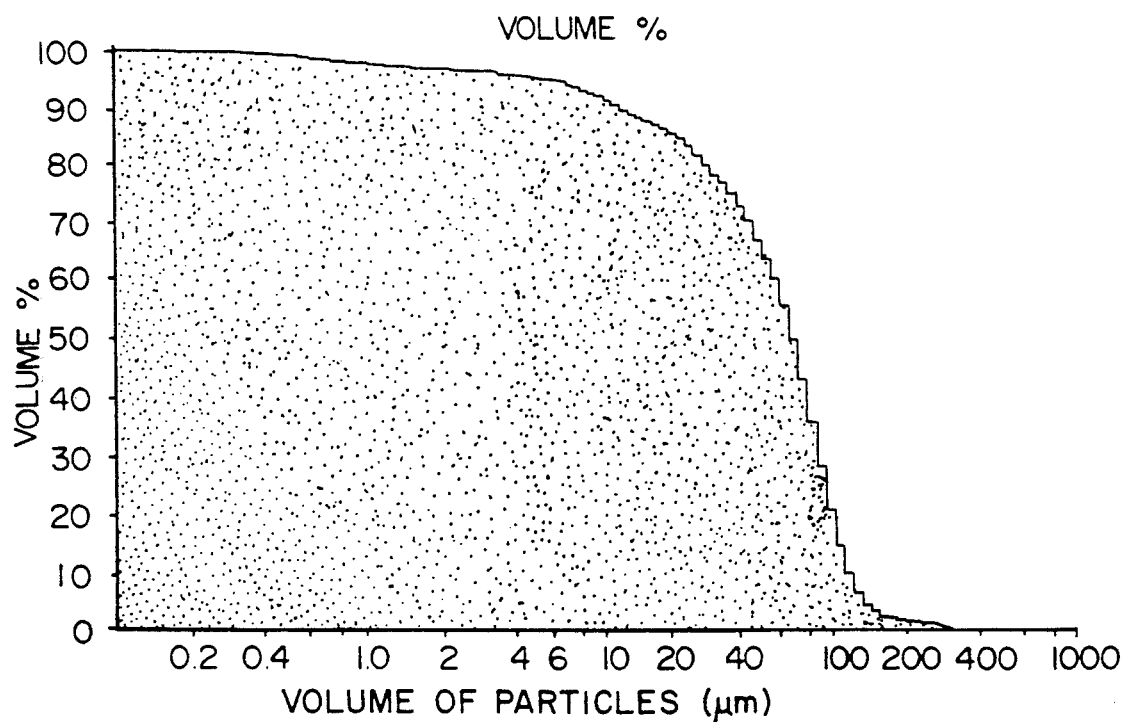
Figure 19A:
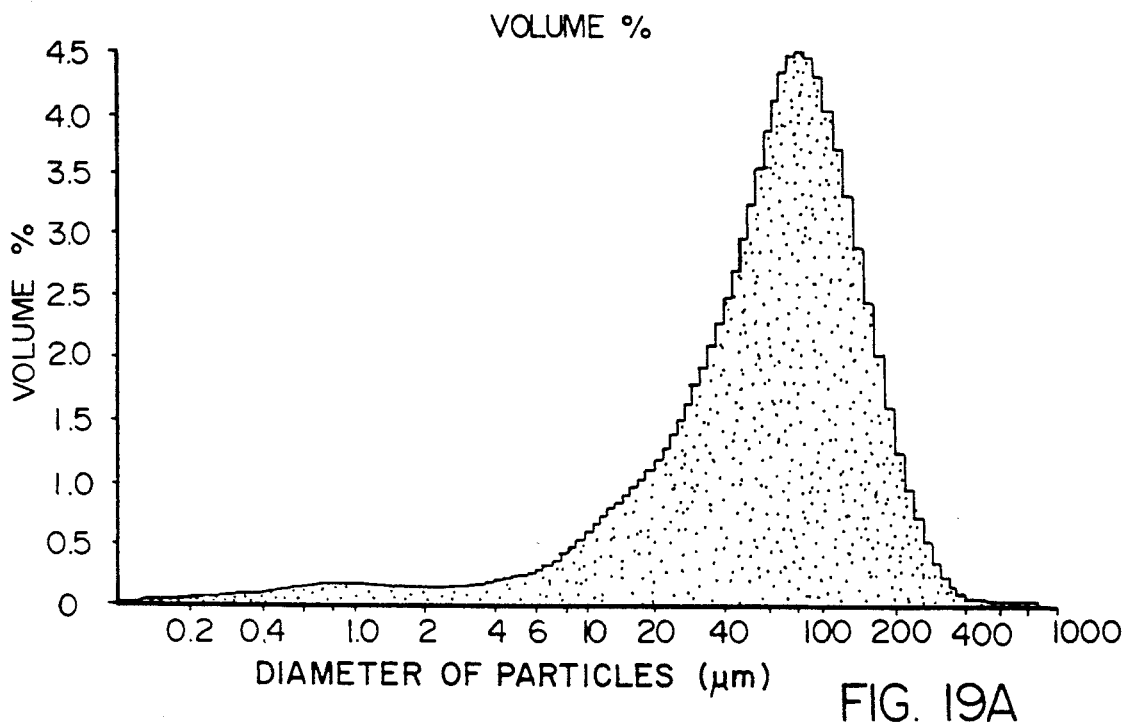
Figure 19B:
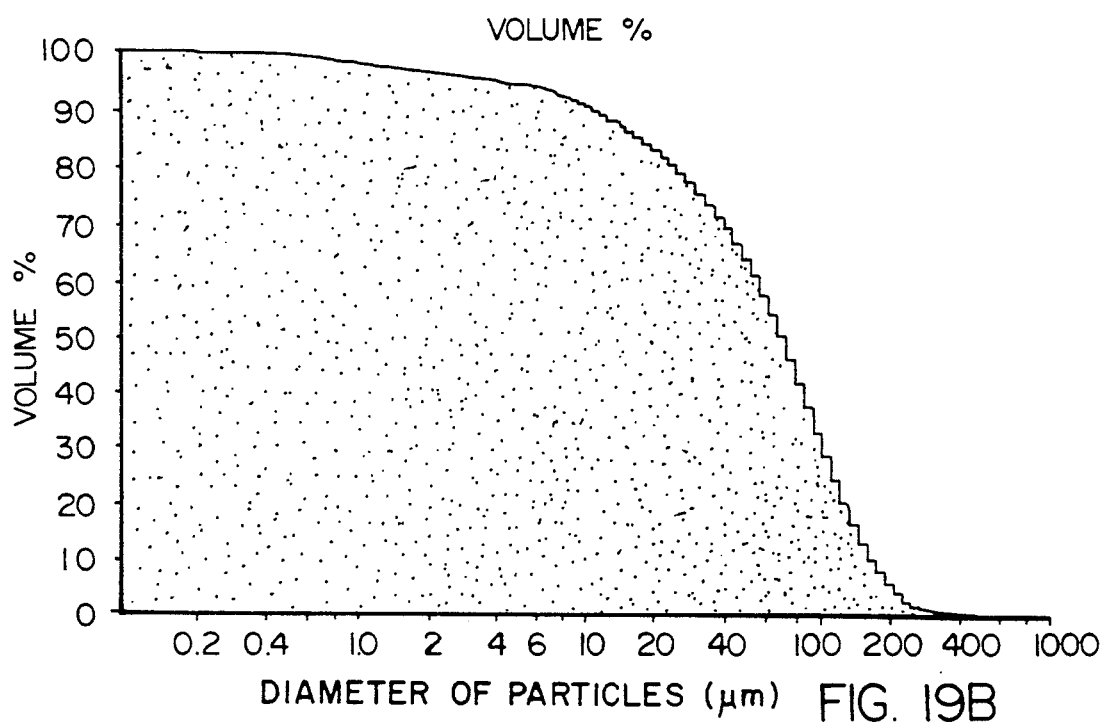
Figure 20A:
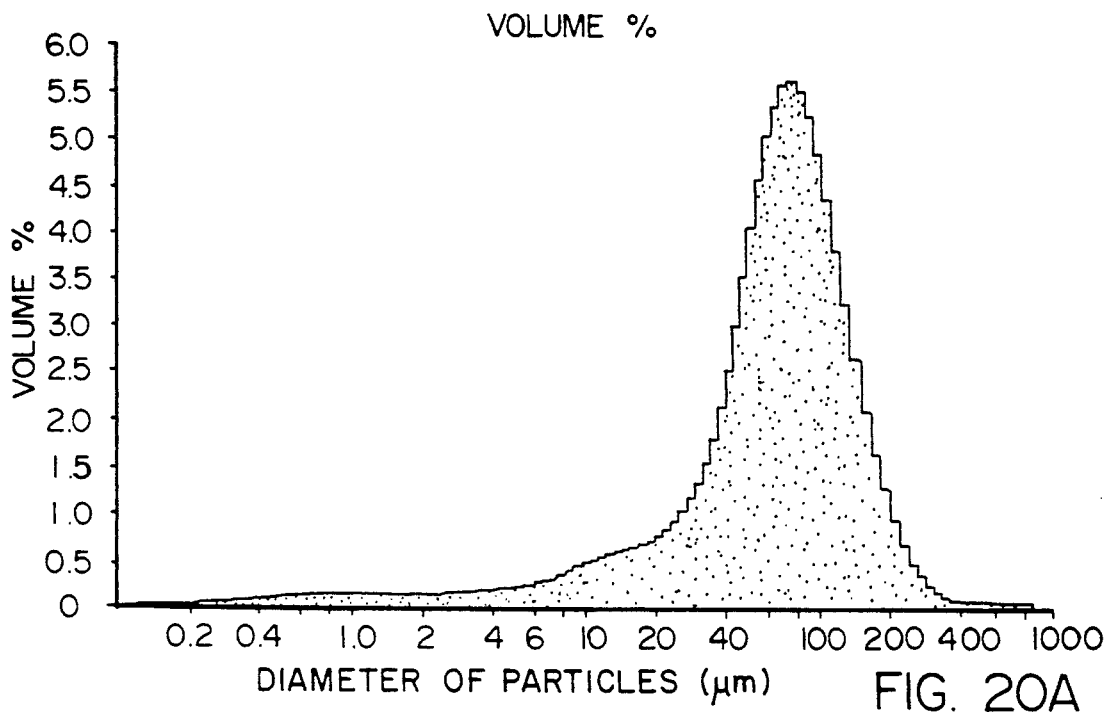
Figure 20B:
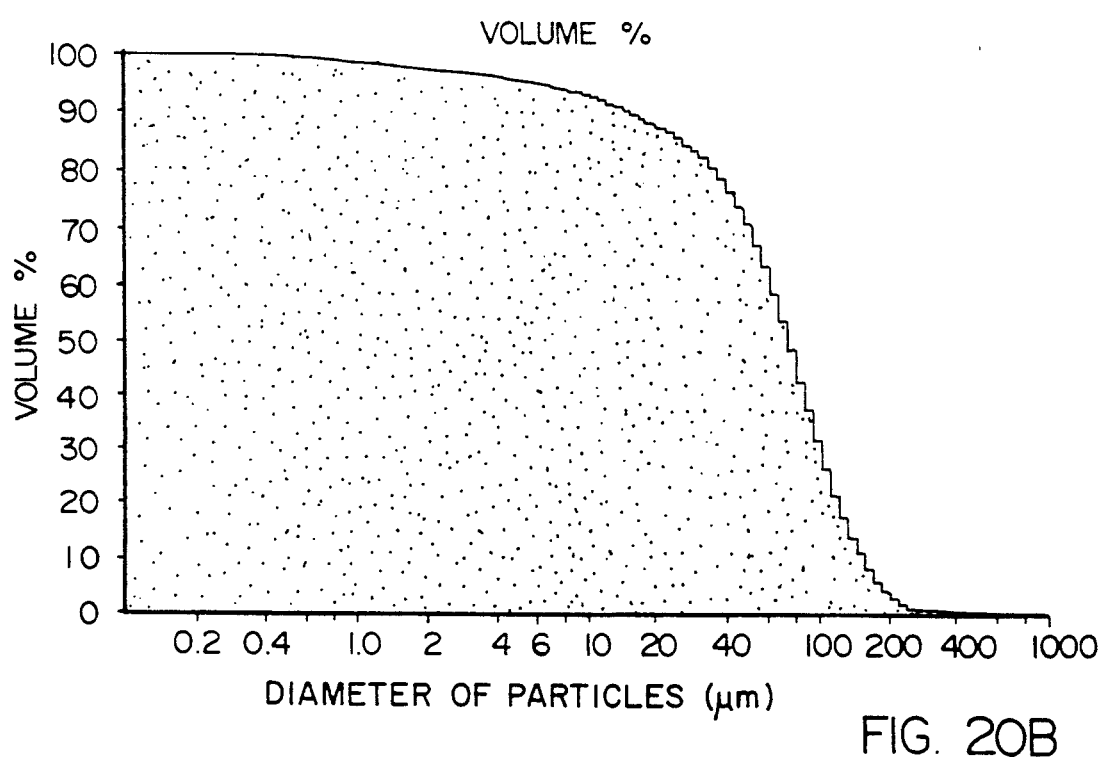

Even an assay with 90 kg (Ref. S4— batch 3) has given the following granulometric analysis (see FIG. 16).

EXAMPLE XIV

Microcrystalls of Progesterone

This study has been performed as in the preceding examples, by dissolving the starting material at the reflux temperature in 6 vol. of a solvent made of:
93.4% ethanol
6.0% water
0.6% TWEEN 40

The thus formed crystals are separated in the cold and washed with water then dried. The thus produced crystals range from 150×80 μm for the bulkiest ones to 10×20 μm for the smallest ones.
MPk=125°±2°
$[\alpha]_D$ (dioxan)= +170°±4°

EXAMPLE XV

Microcrystalls of 17β-Acetoxy 17α-Ethynyl 5α-Δ2-Androsten

As described in the preceding examples, the product has been processed in dissolving it at the reflux temperature in 4 vol. of a mixture made of:
96.0% ethyl acetate
3.2% water
0.8% TWEEN 20

The crystals are recovered as previously described in the preceding examples. The thus produced crystals has a mean granulometry of 40 to 60 μm.
MPk=125°-129°

EXAMPLE XVI

Microcrystalls of Androstanolone (4-Dihydro Testosterone)

The product is processed as in the previously cited examples, in dissolving the starting material at the reflux temperature in 7.5 vol. of a solvent made of:
91.8% methanol
8.0% water
0.2% TWEEN 20

The thus formed crystals are separated in the cold, then are washed with water and dried. The crystals show a mean granulometry of 120 μm.
MPk=182°±2°
$[\alpha]$ (ethanol)= +30°±2°

Figure 8A:
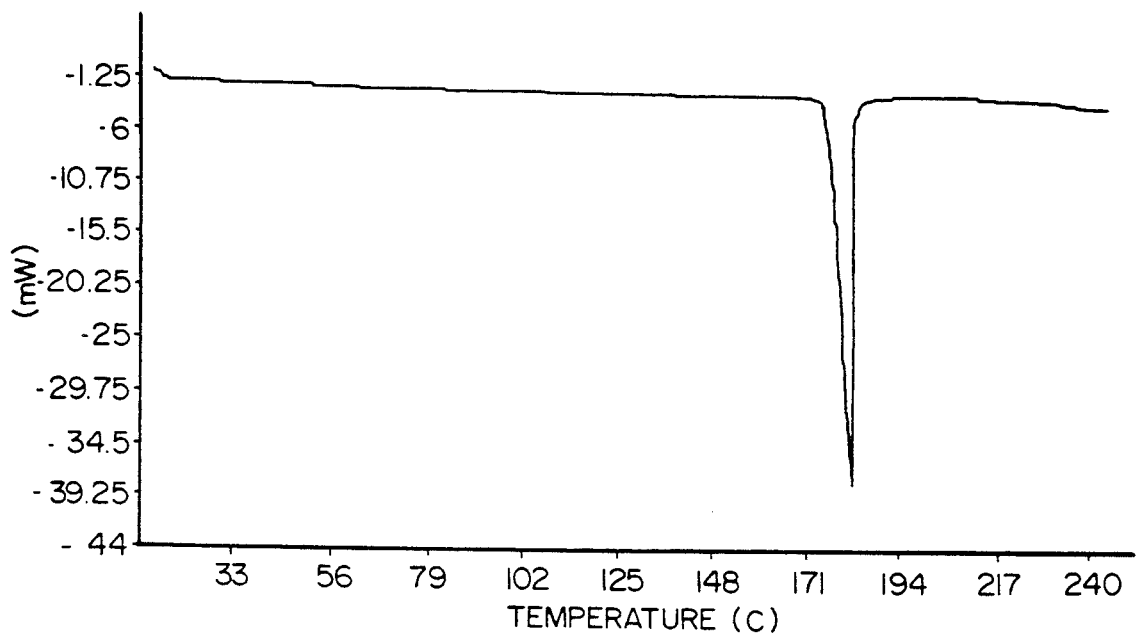
Figure 8B:
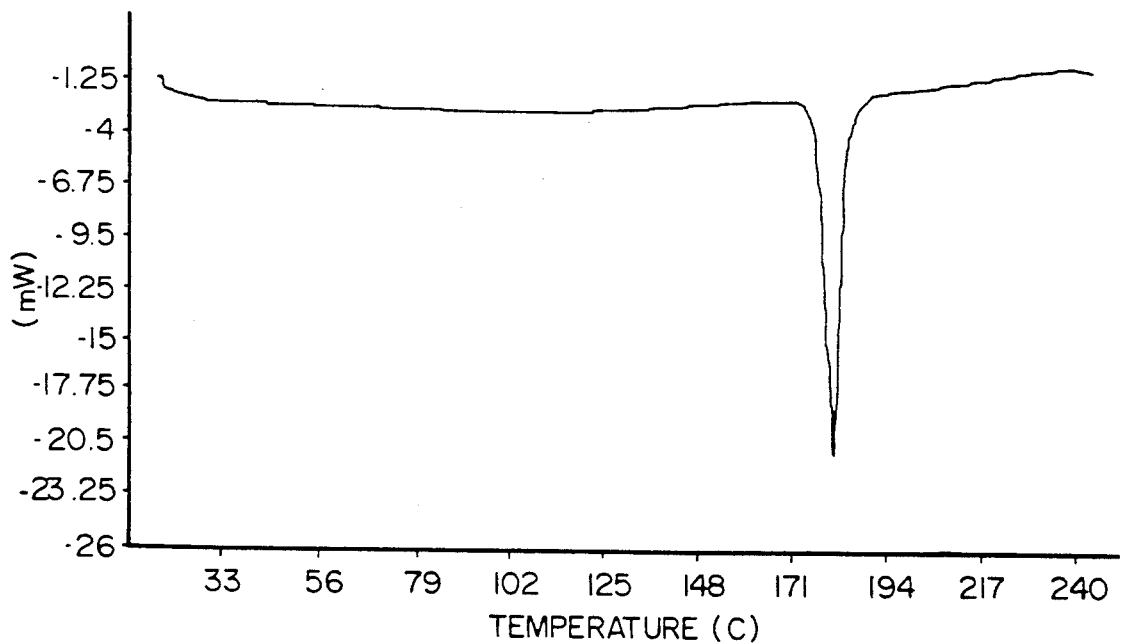
Figure 9A:
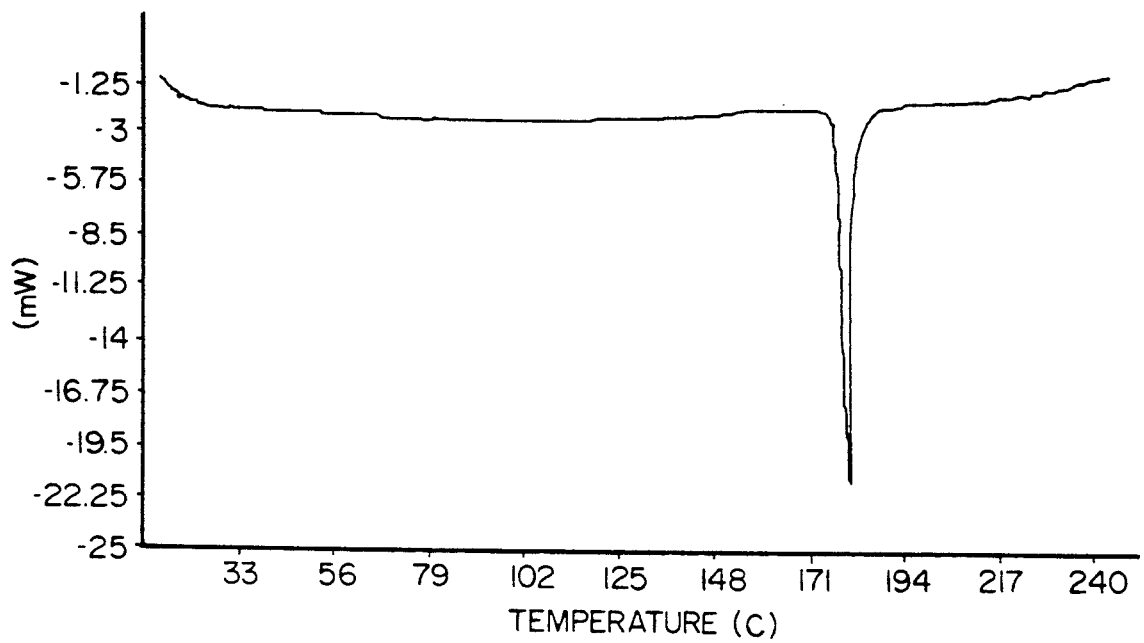
Figure 9B:
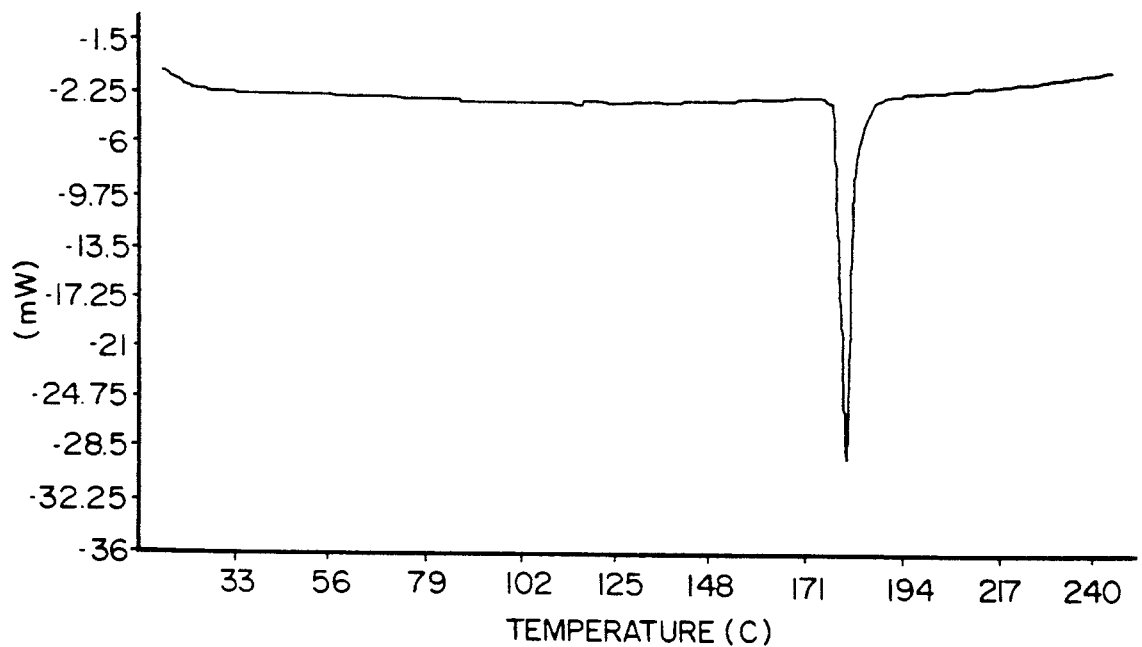

A differential thermic analysis has been performed on industrial batches of Nomegestrol acetate before grinding, after grinding and after microcrystallization:
sample A and B for Nomegestrol acetate before grinding (FIG. 8)
sample C and D for Nomegestrol acetate after grinding (FIG. 9)
samples E and F for Nomegestrol acetate after microcrystallisation The microcrystallization, subject of this invention, has been performed on the raw material before grinding.

RESULTS

The assays temperatures range from 290° to 525° K. It has not been found any solid/solid transition. The solid/liquid transition has been found depending on the sample from 178.1° to 179.1° C.

Figure 1B:
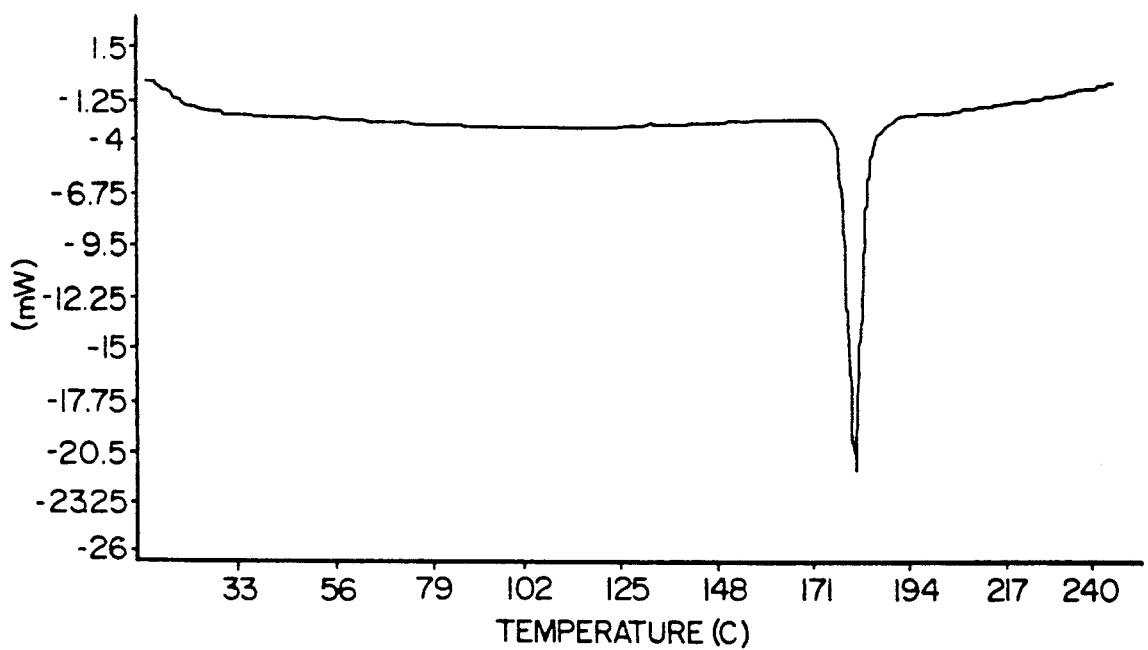
Figure 2A:
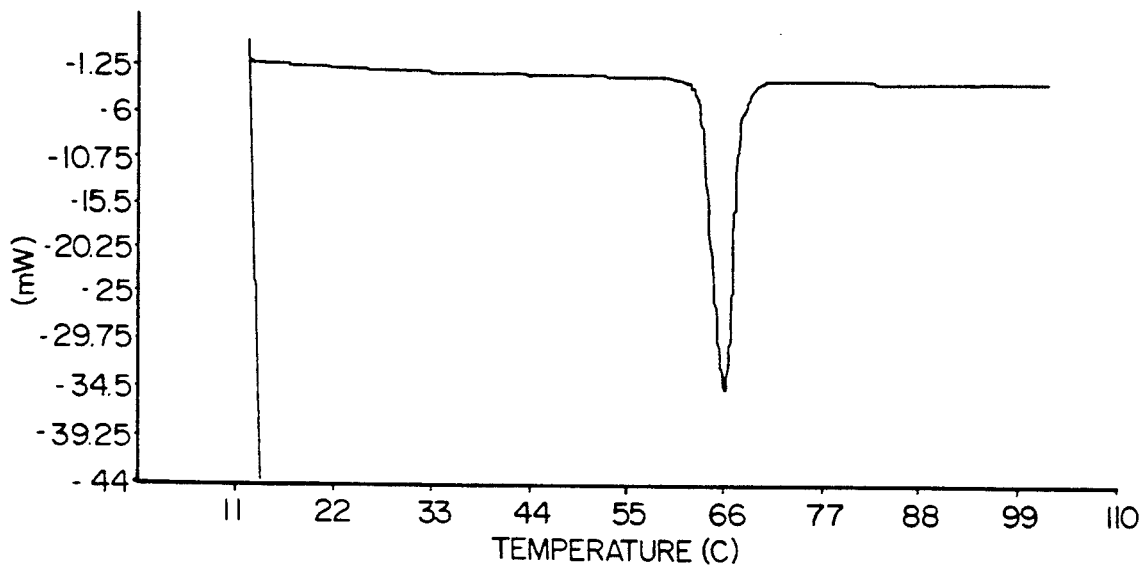
Figure 2B:
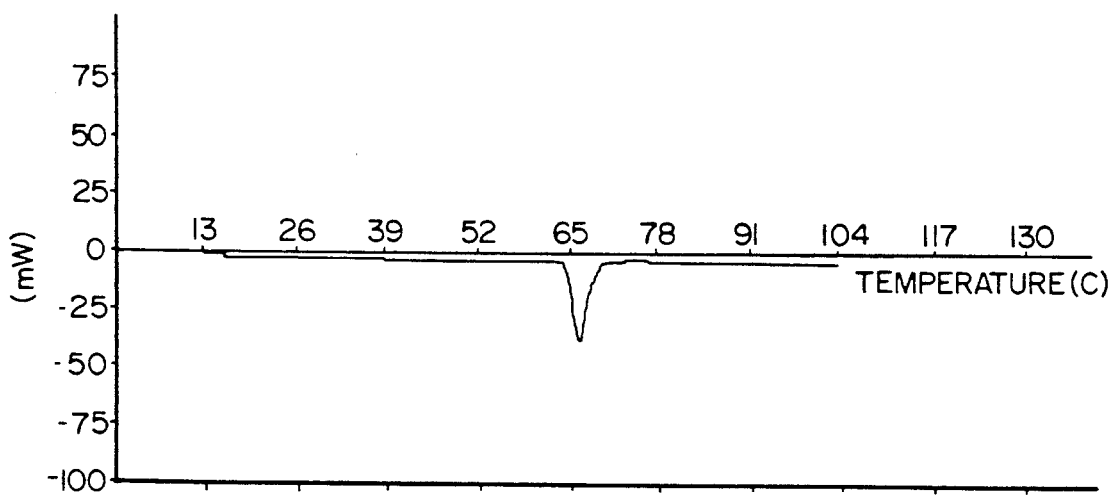
Figure 3A:
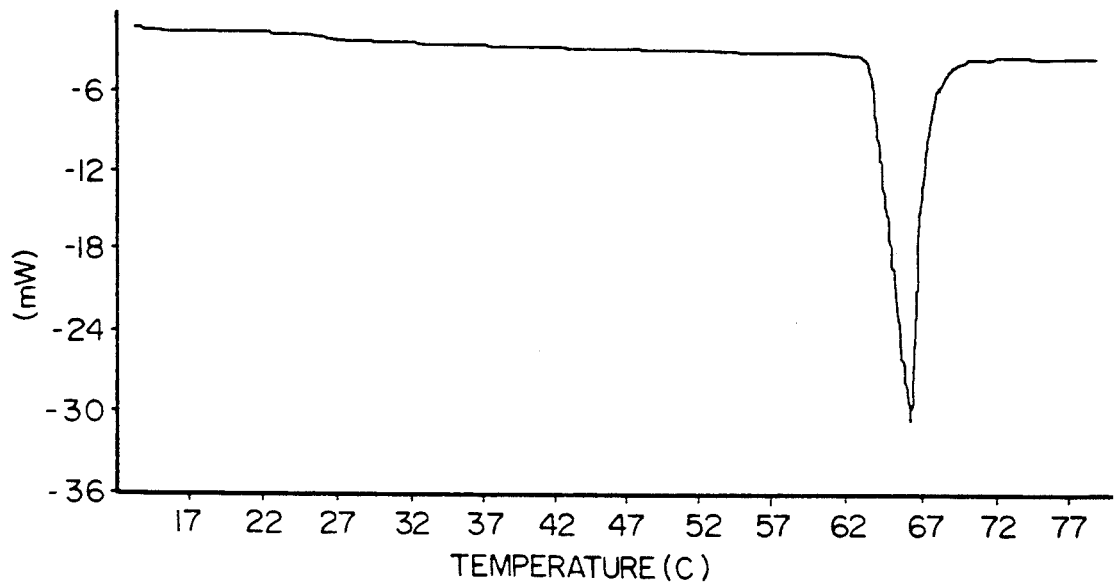
Figure 3B:
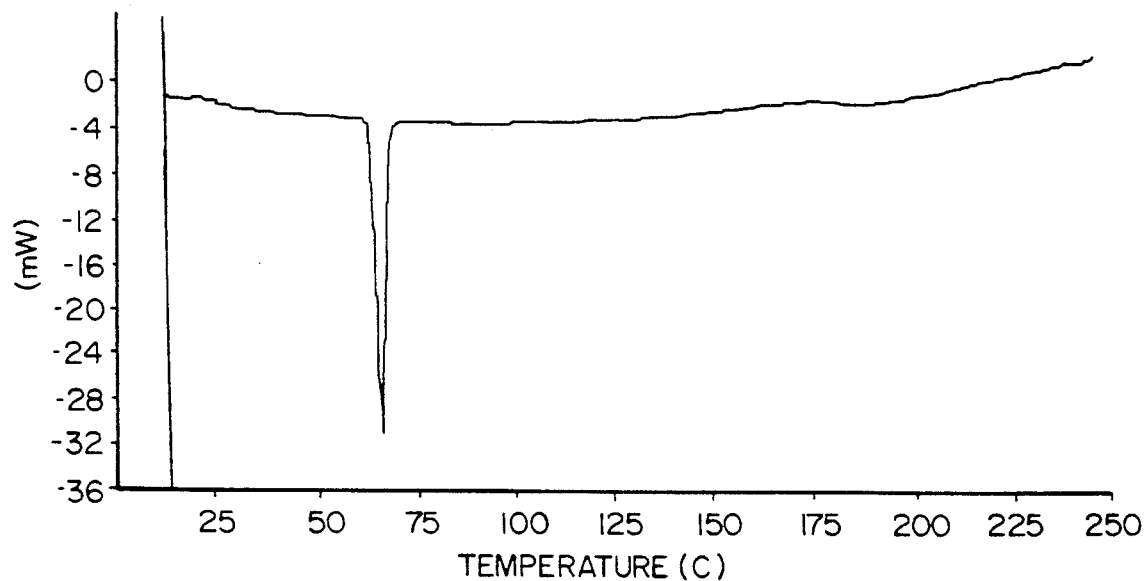
Figure 4:
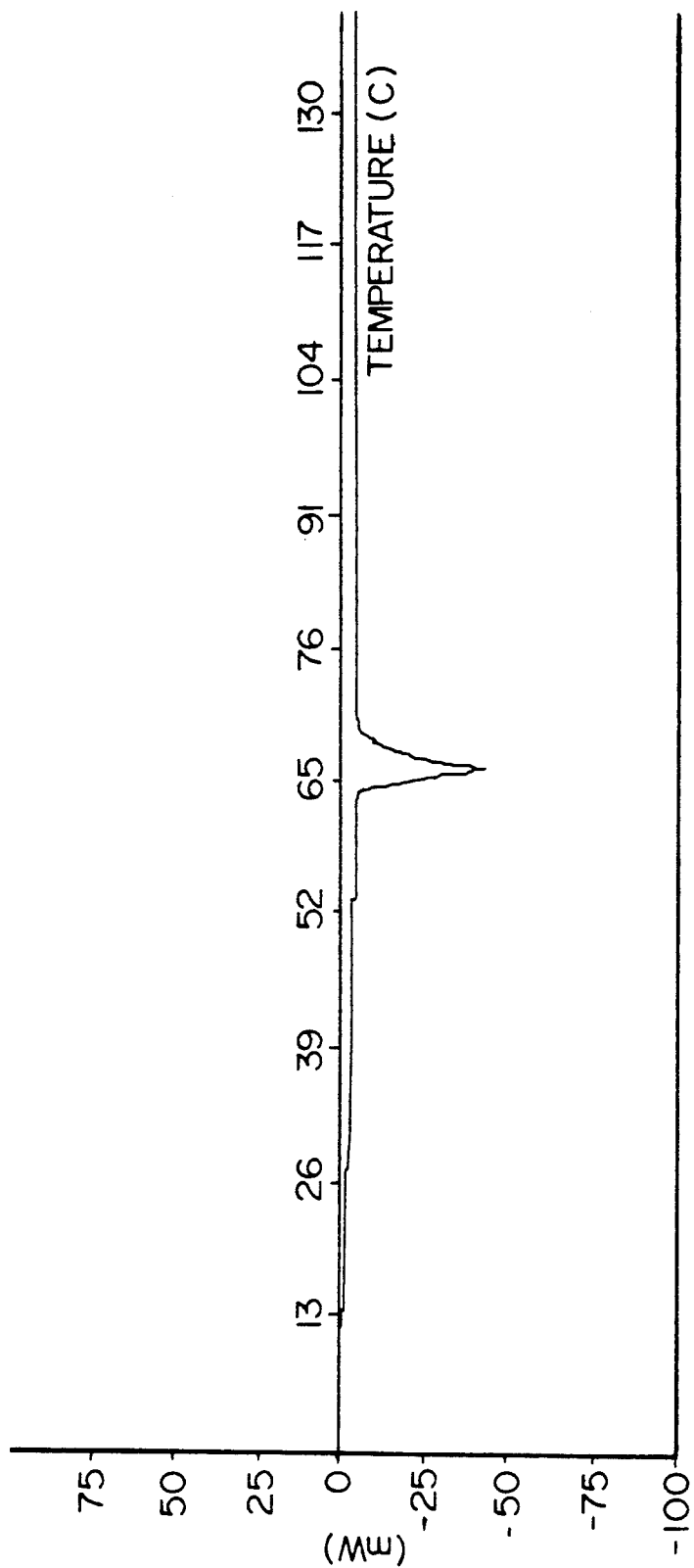
Figure 5A:
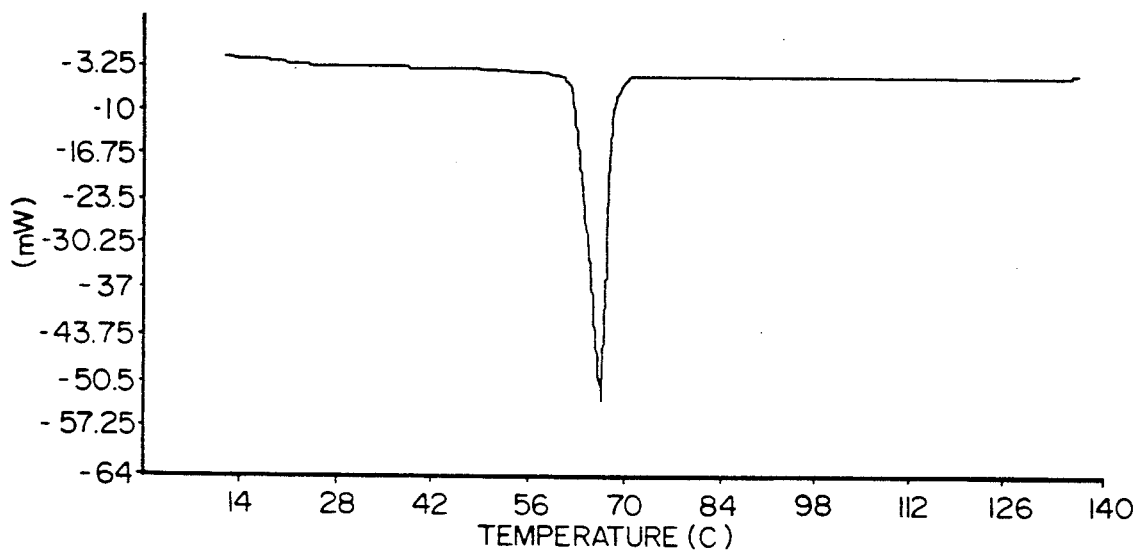
Figure 5B:
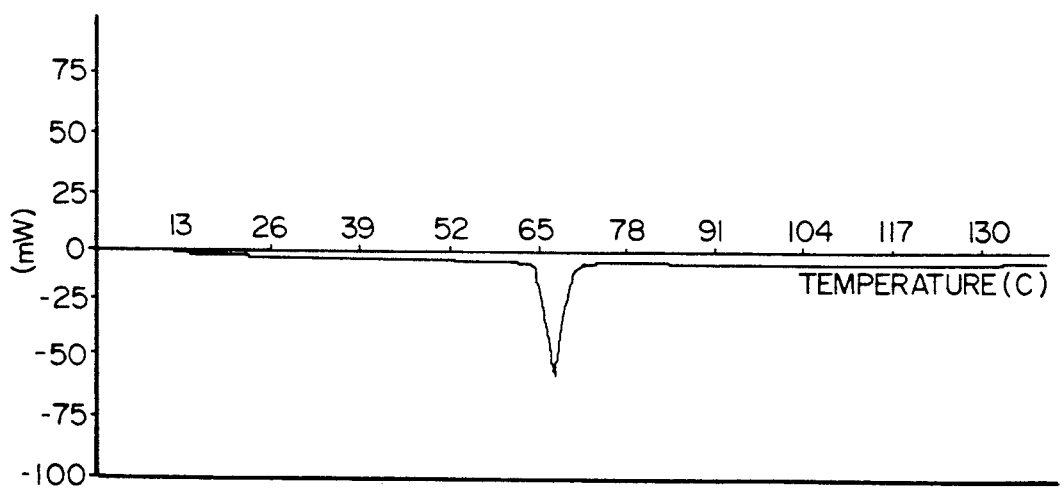
Figure 6:
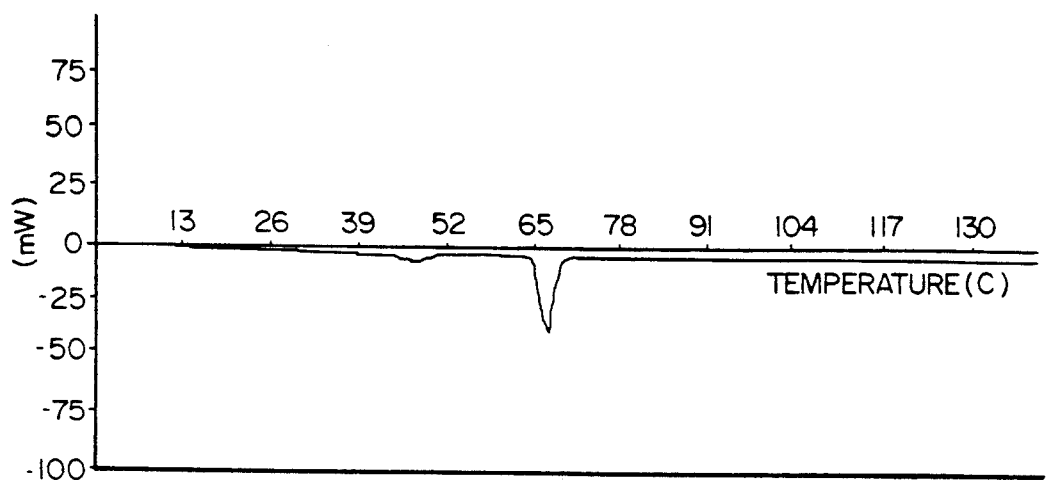

The transition enthalpy is about 6.8 joules/g. The intervals of temperature for the transitions solid/liquid have been found the smallest for the samples E and F, resulting from the microcrystallized compound according to the therein claimed process (FIG. 1).

Figure 10:
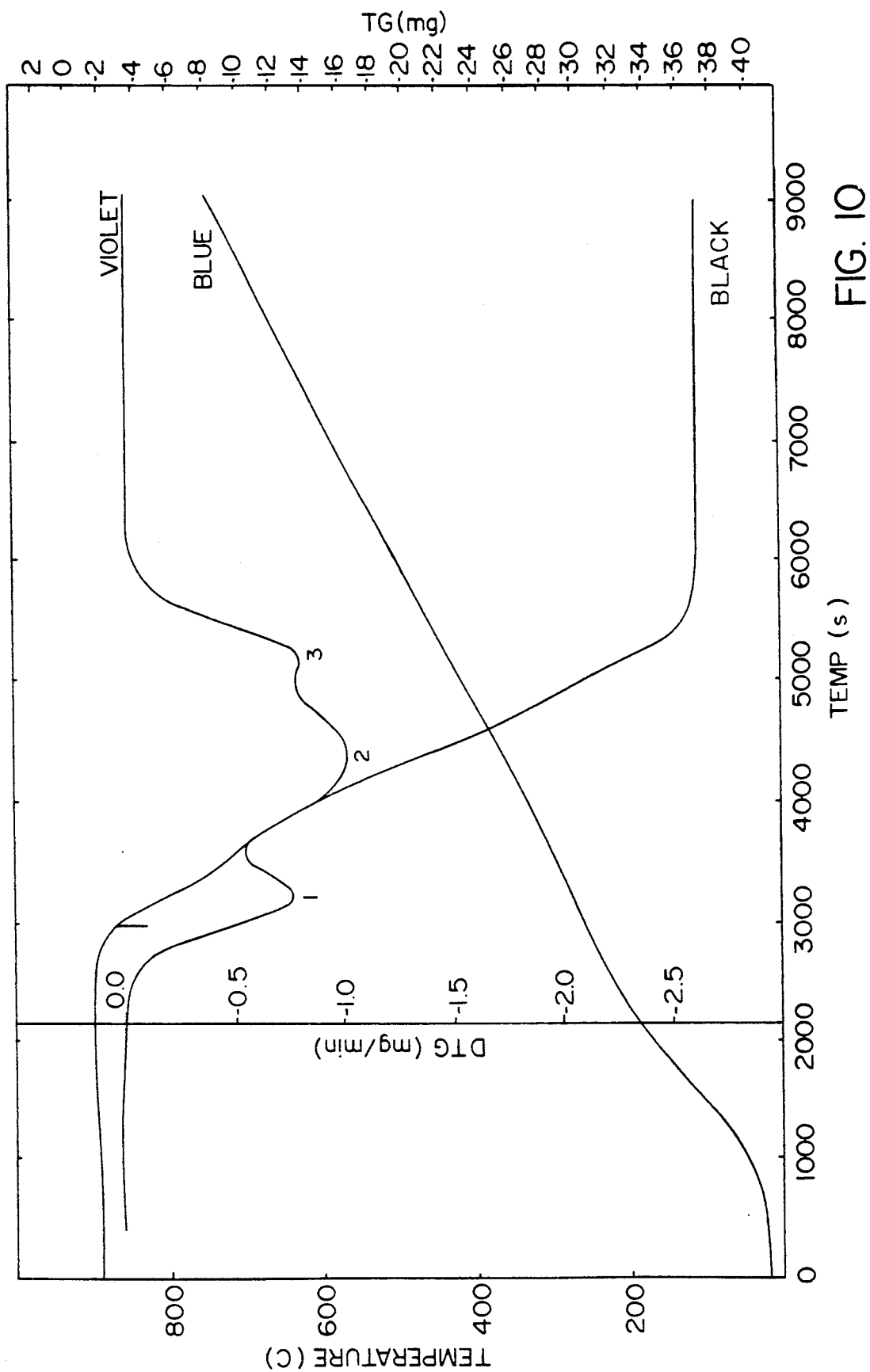

A thermogravimetric analysis has been performed on a sample (B) of starting material. With this kind of product at assay temperatures ranging from 25° to 700° C., the loss of mass is about total at 400° C. (FIG. 10).

It has been also possible to study the granulometric classes resulting from the process of microcrystallization, by means of an image scanner fitted with a logiciel VIDS IV.

On the industrially recrystallized product according to the process of example XII (batch 037 MC 2) it has been performed a study with this kind of material. The obtained results are expressed in μm for the dimensions (parameters and length) and in μm² for the surfaces.

This kind of analysis allows a clear confirmation of the results obtained by Laser granulometry. In a field of small particles, it has been made out particles from 9 to 16 μm, which are values similar to that observed by Laser granulometry.

Analysis of the bulkiest particles has supplied with dimensions close to 70 μm, values also obtained with Laser granulometer.

The chromatographic analysis by HPLC allows to show the baneful influence of the grinding. For Nomegestrol acetate the damaging may be evaluated to about 0.2%.

Some examples of industrial batches evidence this phenomena:
batches before grinding (Ref. 028 and 031)—(see FIG. 13)
batches after grinding (Ref. 028B and 031B)—(see FIG. 13)

The analysis by HPLC have been carried out at two disterict wawe lenghthes (245 and 290 nm) to have a better separation of the impurities of the type 3-keto Δ-4 pregnene from that of the type 3-keto Δ4,6-pregnadien.

To overcome this damaging, several methods have been contemplated:
one consisting in grinding while cooling the apparatus
the other one using the method of crystallization according to this invention.

In order to be comparative and to be able to validate the method according to this invention, both techniques have been put into practice on a same batch of active ingredient

SCHEME OF THE STUDY

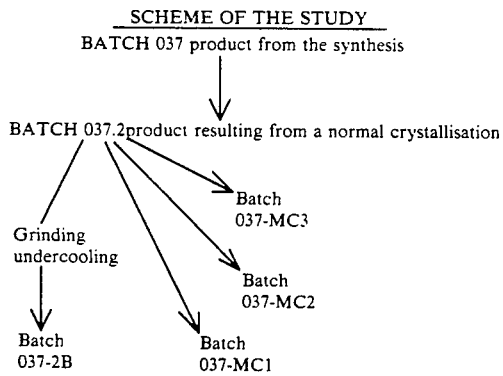

Figure 7:
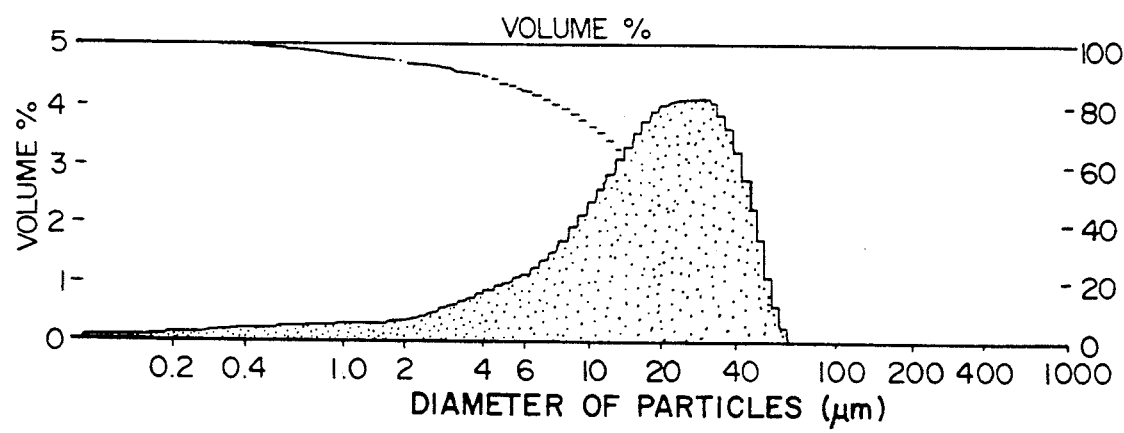
Figure 11:
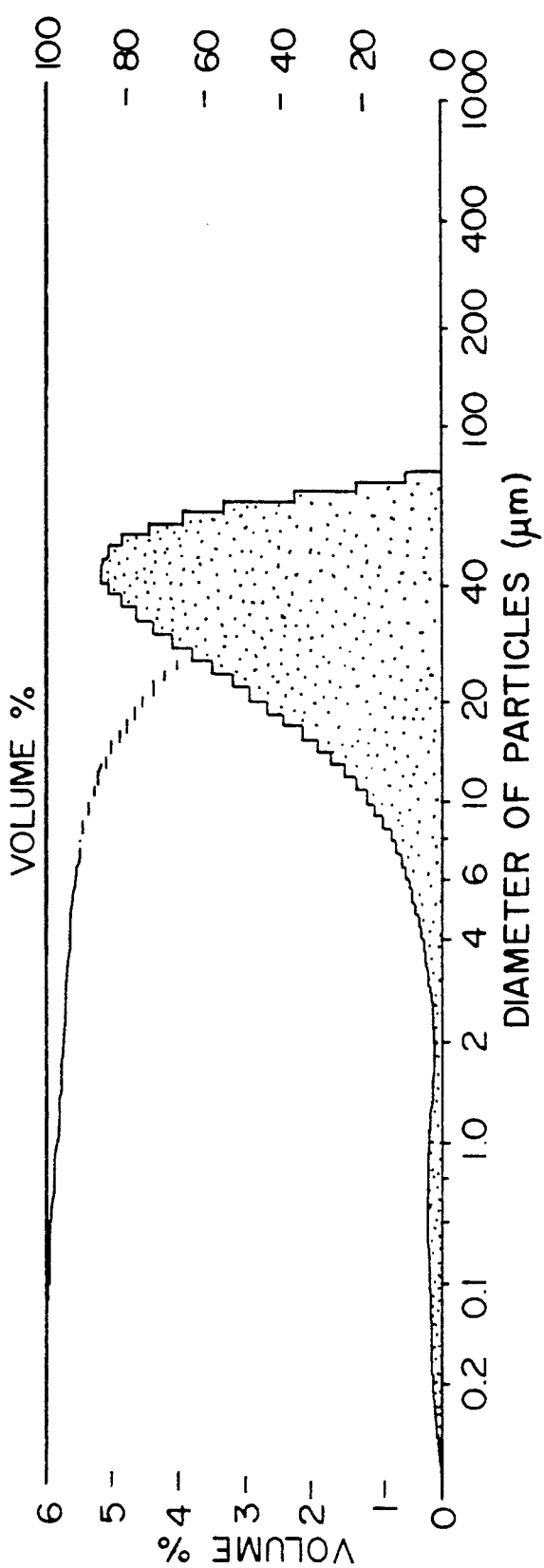
Figure 12:
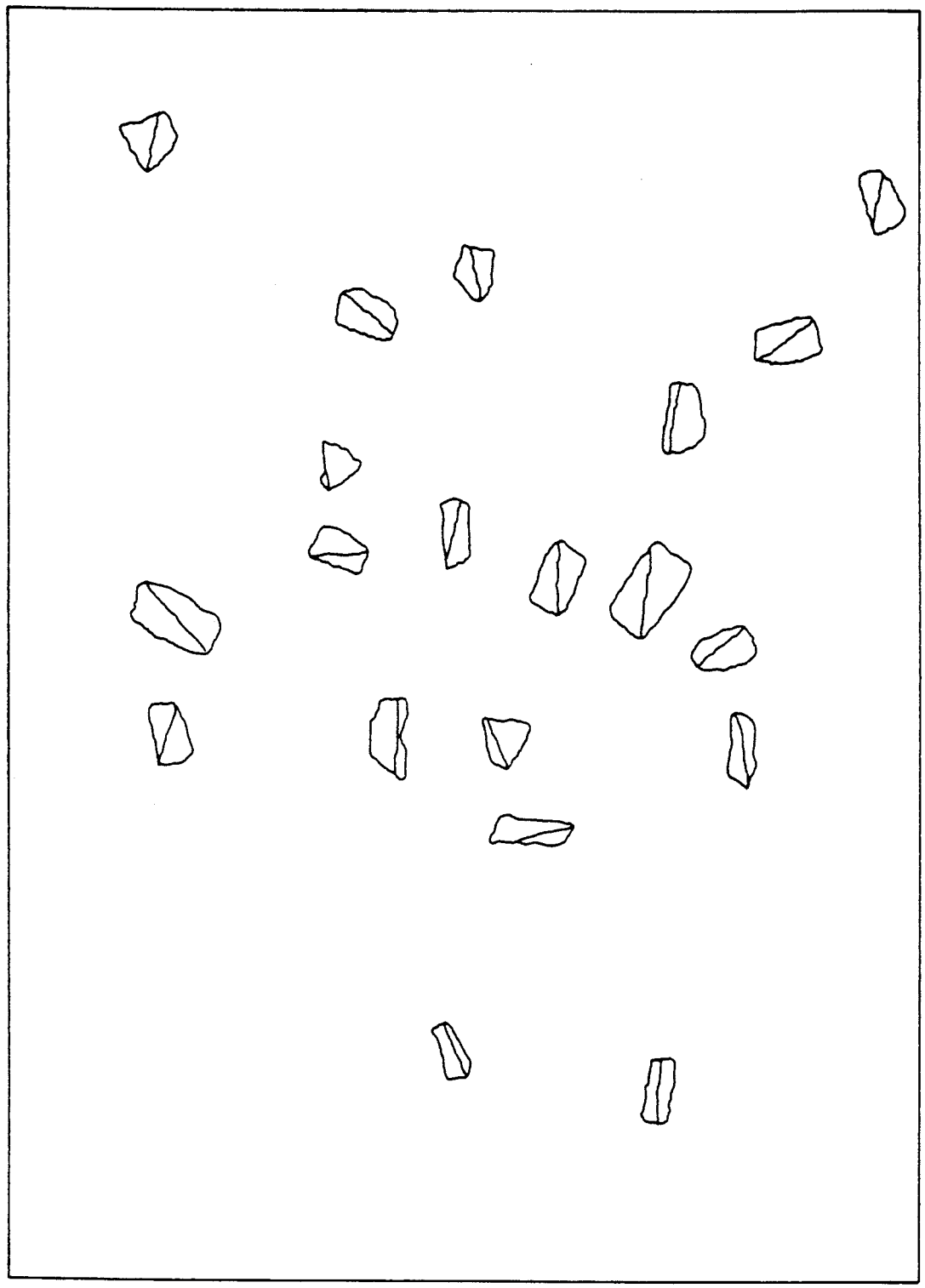

The batches designated as 037-MC 1 a 3 are three assays of recrystallization on industrial batches (30 kg) in order to confirm the validity of the disclosed method, as regard to the granulometric class (FIGS. 7,11 and 12).

The HPLC analysis on the so produced compounds have been performed under the same conditions than those previously described.

Figure 14A:
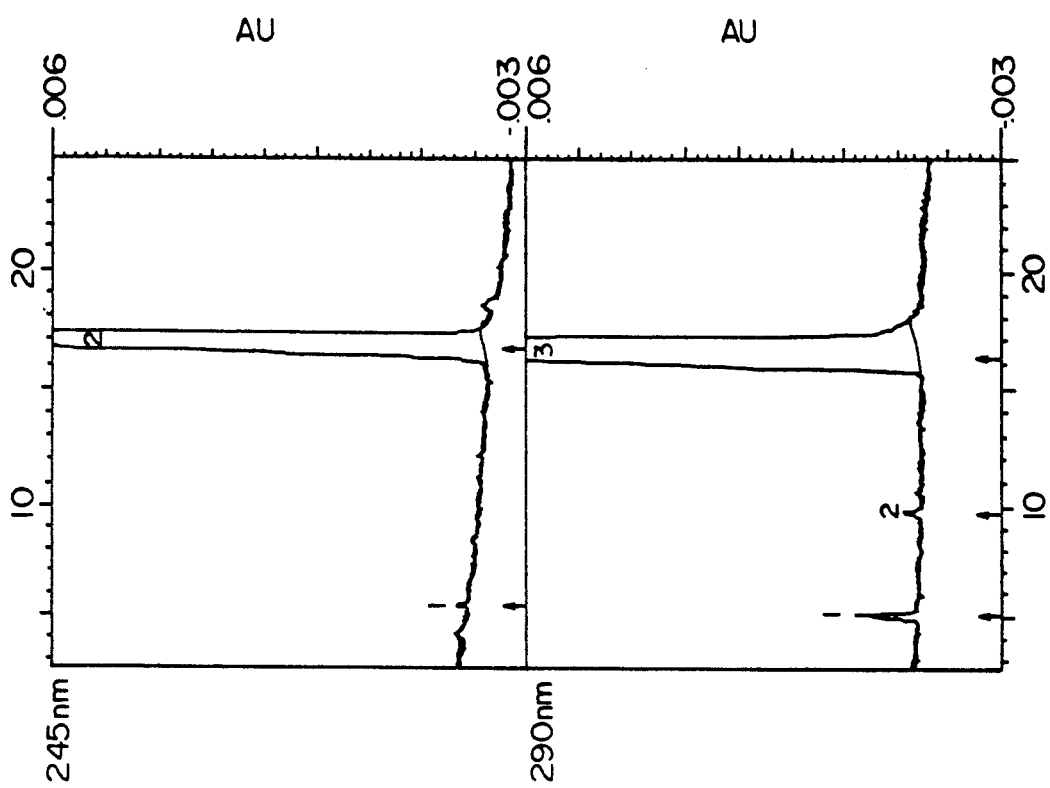
Figure 14B:
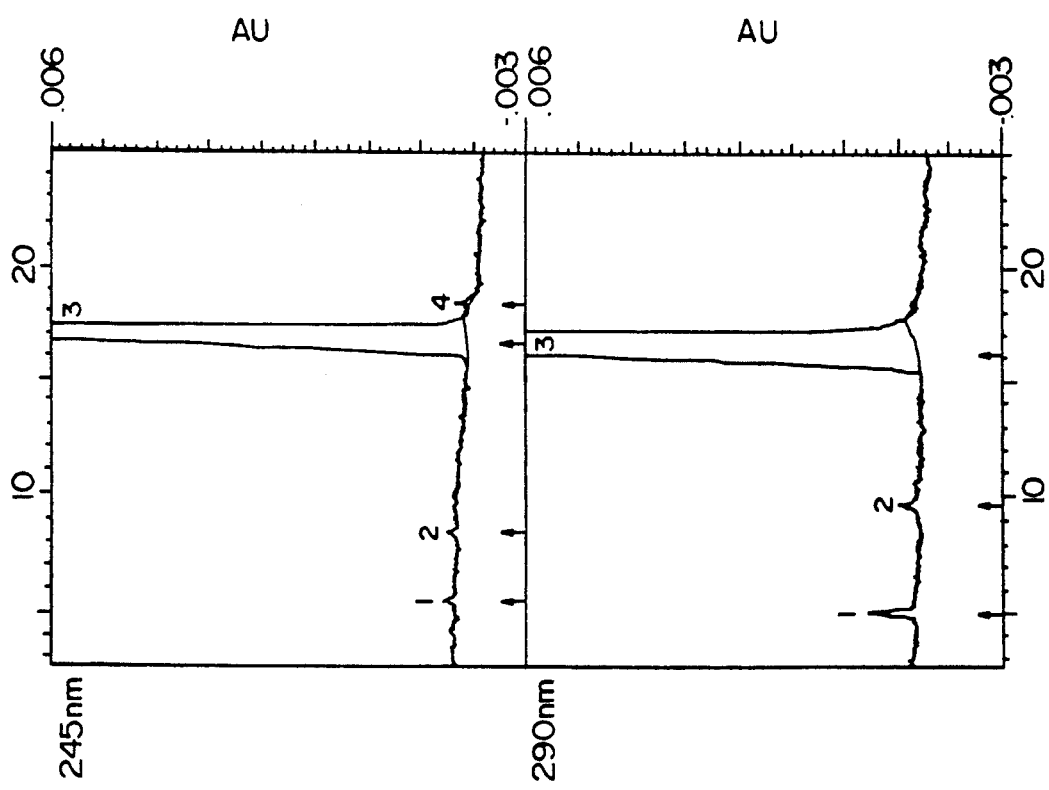

These tests fully demonstrate that:
the grinding, even performed under cooling, does not prevent that the compound fall into disrepair (cf. FIG. 14).
the crystallization according to the process of this invention, allows to obtain an active ingredient of better quality and that in the wanted granulometric class without the need to recurse to a grinding method (FIG. 15).

This phenomenon of chemical alteration is also stated on other steroidal compounds to a more or less extent, depending on the considered active ingredient.

The following examples related to formulations illustrate the use of the microcrystallized compounds of this invention and more particularly of the compounds derived from pregnane.

The disclosed granulometric class is the most representative of the cited compound (i.e. >80%).

EXAMPLE XVII

Tablets with Belated Release

Unit formulation for various dosologies

| | |
|---|---|
| microcrystallized Nomegestrol acetate (200 to 300 μm) from | 1.25 to 10.00 mg |
| Aerosil 200 | 0.37 to 0.50 mg |
| Precirol ATO 5 | 1.85 to 2.25 mg |
| Methocel E.4 | 55.0 to 70.00 mg |
| Avicel PH 101 | 10.00 to 20.00 mg |
| Lactose enough for 1 tablet of | 185.00 to 200.00 mg |

EXAMPLE XVIII

Tablets with Fast Release

Unit formulation for various dosologies

| | |
|---|---|
| microcrystallized Nomegestrol acetate (<50 μm) | 1.25 to 10.00 mg |
| Aerosil 200 | 0.37 to 0.50 mg |
| Precirol ATO 5 | 1.85 to 2.00 mg |
| Avicel PH 102 | 50.00 to 70.00 mg |
| Explotab or Polyplasdone XL | 5.00 to 25.00 mg |
| Lactose enough for a tablet of | 185 to 225.00 mg |

EXAMPLE XIX

Tablets of Nomegestrol Acetate

Unit formulation for various dosologies

| | |
|---|---|
| microcrystallized Nomegestrol acetate (200 to 300 μm) | 1.25 to 10.00 mg |
| Aerosil 200 | 0.37 to 0.50 mg |
| Precirol ATO 5 | 1.85 to 2.25 mg |
| Avicel PH 101 | 55.00 to 70.00 mg |
| Lactose enough for a tablet of | 185.00 to 220.00 mg |

The analysis of the results by the function of distribution of Weibull(D. GIBASSIER and COWORK—STP PHARMA 1(10) (1985) 967–973) evidence a significant difference between these three formulations.

The shapes of dissolution curves, as shown by the parameter $\beta$ of this function, give 0.148 for a formulation with fast release, 1.015 for a formulation with normal release and 1.914 for a formulation with delayed release (cf. FIG. 21).

The process of this invention thus allows the realization of granulometric classes of an active ingredient appropriate to the needs of the formulation to be realized.

It is ascertained that these two pharmaceutical compositions which have been realized from industrial raw materials, have an equivalent bioavailability.

EXAMPLE XX

Injectible depot formulation based on Medroxyprogesterone or on Nomegestrol in the form of their acetates.

Unit formulation for 1 flask of 5 ml:

| | |
|---|---|
| microcrystallized Medroxy progesterone acetate or microcrystallized Nomegestrol acetate (15 to 40 μm) | 500.00 mg |
| Polyethylene glycol 4000 | 200.00 mg |
| Preservatives | 0.006 mg |
| Sodium chloride/Sodium Citrate | 0.15 mg |
| Distilled water for injection | 5.00 mg |

EXAMPLE XXI

Vaginal or Gynaecologic Capsule a) unit formulation for a capsule

| | |
|---|---|
| microcrystallized progesterone (200 to 300 μm) | 50 to 500.00 mg |
| Vaseline (pharmacopeia) | 200.00 mg |
| Sorbitol sesquioleate | 200.00 mg |
| Synthetic perhydrosqualene | 1.85 g |

Dry coating: gelatine, glycerol, preservative, for a soft gelatine capsule weighing 2.55 g b) vaginal suppository

| | |
|---|---|
| microcrystallized Nomegestrol acetate | 20.00 mg |
| vithepsol H35 or H37 enough for a suppository of | 2.8 g |

EXAMPLE XXI

Bioadhesive Gel for Cutaneous or Gynaecologic Use

Formula for 100 g:

| | |
|---|---|
| microcrystallized Progesterone | 2.0 to 3.0 g |
| Polyethylene glycol | 4.0 to 6.0 g |
| Carboxypolyvinyl polymer | 0.5 to 1.0 g |
| Preservatives | 0.3 mg |
| Triethanolamine enough for pH 6.5 | |
| Purified water | 100.0 g |

EXAMPLE XXIII

Bioadhesive Gynaecologic Foam Formula for a Dispenser (2.5 ml) of 50 g

| | |
|---|---|
| microcrystallized Progesterone | 2.0 to 5.0 g |
| Carboxypolyvinyl polymer | 0.5% |
| Isobutane | 5.5% |
| Excipient base F25/1 enough for | 50.0 g |

Shake the suspension before use.
Dispensed dosage from 100 to 250 mg.

EXAMPLE XXIV

Implants

Formulation for 100 g of material to be extruded:

| | |
|---|---|
| Nomegestrol acetate | 5.0 g |
| Poly (orthocarbonates) enough for | 100.0 g |

The temperature of the mixture shall not excede 185° C. in order not to impair the crystalline form of the active ingredient.

EXAMPLE XXV

Intra-uterine Device with Reservoir

Device with a Silastic reservoir of 2.5 to 3.5 cm length for a thickness of 0.4 to 0.8 mm and a diameter of 2 mm.

The preparation is formulated as a suspension as follows:

For 100 g of suspension:

| | |
|---|---|
| microcrystallized Progesterone (80-250 μm) suspended into | 0.600 to 1.0 g |
| suspending agent | 0.5 g |
| synthetic Perhydrosqualene | 100.0 g |

EXAMPLE XXVI

Patches

Content of the reservoir. Preparation for 100 g:

| | |
|---|---|
| microcrystallized Nomegestrol acetate (80–250 μm) | 0.5 g |
| Carboxy polyvinylic polymer | 0.2 g |
| Colloidal silica | 0.2 g |
| Silicone oil enough for | 100.0 g |

Examples of Formulation of Estrane Derivatives

EXAMPLE XXVII

Tablets

Unit formulation:

| | |
|---|---|
| microcrystallized Estradiol (10–50 μm) | 1.0 to 2.0 mg |
| Kollidone 25 | 10.0 to 20.0 mg |
| Kollidon 90 | 5.0 to 10.0 mg |
| Avicel PH 102 | 25.0 to 50.0 mg |
| PEG 6000 | 1.0 to 2.0 mg |
| Precirol ATO 5 | 1.5 to 3.0 mg |
| Polyplasdone XL | 2.5 to 5.0 mg |
| Lactose enough for 1 tablet | |

EXAMPLE XXVIII

Bioadhesive Gels based on Estradiol or Promestriene

Formulation for 100 g of gel:

| | |
|---|---|
| microcrystallized Estradiol or Promestriene | 1.0 to 2.0 g |
| Propylene glycol | 5.0 to 10.0 g |
| Carboxypolyvinyl polymer | 0.5 to 1.0 g |
| Preservatives | 0.3 mg |
| Triethanolamine enough for pH | 6.0 to 6.5 |
| Purified water enough for | 100.0 g |

EXAMPLE XXIX

Vaginal Capsules

Formulation for one capsule:

| | |
|---|---|
| microcrystallized Estradiol | 1.0 mg |
| Labrafil M 1944 CS | 0.5 g |
| Perhydrosqualene | 1.3 g |

Dry coating: gelatine, glycerol, preservatives for a soft gelatine capsule of 2.1 g

EXAMPLE XXX

Patches

Content of the reservoir: formula for 100 g

| | |
|---|---|
| microcrystallized Estradiol (80–100 μm) | 0.5 to 1.0 g |
| Aerosil | 0.5 g |
| synthetic Perhydrosqualene enough for | 100.0 g |

EXAMPLES OF FORMULATION WITH COMPOUNDS DERIVED FROM ANDROSTANE

EXAMPLE XXXI

Formulation as tablets-unit formulation for a 380 mg tablet:

| | |
|---|---|
| microcrystallized 17β-acetoxy 17α-ethynyl 5α-androst-2en | 20.0 mg |
| Avicel PH 101 | 91.20 mg |
| Aerosil | 0.45 mg |
| Precirol ATO 5 | 7.60 mg |
| Explotab | 4.30 mg |
| Lactose | 256.45 mg |

This formulation shows a better availability than that previously disclosed in the literature.

EXAMPLE XXXII

Gynaecologic Gel

Formulation for 100 g:

| | |
|---|---|
| microcrystallized Androstanolone (dihydrotestosterone) | 2.50 g |
| Propylene glycol | 2.50 g |
| Transcutol | 5.00 g |
| Preservatives | 0.08 g |
| Viscosity agent (such as TEA) | 0.25 g |
| Carboxypolyvinyl polymers | 1.50 g |
| Purified water enough for | 100.00 g |

EXAMPLE XXXIII

Oral Capsule

| | |
|---|---|
| microcrystallized Testosterone Heptylate | 50.00 mg |
| Oleic acid enough for 1 capsule | 250.00 mg |

Coating: gelatine, preservatives, glycerol

EXAMPLES OF FORMULATION WITH COMPOUNDS DERIVED FROM 21-HYDROXY PREGNENES

EXAMPLE XXXIV

Tablets for the Oral Way

Unitary formulation for each tablet:

| | |
|---|---|
| microcrystallized Prednisone (80–150 μm) | 2.50 mg |
| Avicel PH 102 | 50.00 mg |
| Aerosil | 1.80 mg |
| Precirol ATO 5 | 2.00 mg |
| Lactose enough for one tablet | 128.70 mg |

EXAMPLE XXXV

Tablets for the Oral Way

Unitary formulation for each tablet:

| | |
|---|---|
| microcrystallized Prednisone (80–150 μm) | 0.50 mg |
| Avicel PH 102 | 50.00 mg |
| Aerosil | 1.70 mg |
| Precirol ATO 5 | 2.00 mg |
| Lactose enough for on tablet | 130 mg |

EXAMPLE XXXVI

Gel for Cutaneous Application

Formulation for 100 g:

| | |
|---|---|
| microcrystallized Dexamethasone acetate | 0.05 to 0.10 g |
| Polyethylene glycol | 5.00 g |
| Carboxypolyvinyl Polymer | 1.00 g |
| Triethanolamine enough for pH | 6.5 |
| Purified water enough for | 100.0 g |

EXAMPLE XXXVII

INJECTIBLE SUSPENSION

Unit formulation for a 2 ml ampul:

| | |
|---|---|
| microcrystallized Dexamethasone acetate (>80 μm) | 10.0 mg |

Suspension solution:

| | |
|---|---|
| Polysorbate 80 | 0.015 g |
| Sodium carboxymethyl cellulose | 0.010 g |
| Sodium chloride | 0.010 g |
| Purified water for injection enough for | 2.00 ml |

FIG. 1

| DEE C108B | |
|---|---|
| Initial temperature: | 285.2K |
| Final temperature: | 379.3K |
| Scanning rate: | 2.00 C/mn |
| Amplification range: | 1.000 mV |
| Sample mass: | 37.200 mg |
| Sampling rate: | 2.08 s |
| Storage: | 1357 points |

FIG. 2

| Glass transition determination | |
|---|---|
| Temperature range for Tg Determination: | |
| Beginning temperature: | 61.79 C. |
| End temperature: | 66.63 C. |
| The three Glass temperatures are: | 64.0 C. |
| | 64.79 C. |
| | 65.38 C. |
| Cp variation: | 6.64 Cal/g C. |
| Integration with a linear base line | |
| Peak start: | 62.06 C. |
| Peak end: | 74.23 C. |

-continued

| | |
|---|---|
| Onset temperature: | 64.89 C. |
| Enthalpy: | −.27672E + 004 mJ or −.66202E/003 mcal |
| | −.74389E + 002 J/g or −.17796E + 002 cal/g |
| Endothermic peak | |
| top of peak temperature: | 66.56 C. |

FIG. 3

01/08/90
DEE C114B

| | |
|---|---|
| Initial temperature: | 285.2K |
| Final temperature: | 525.0K |
| Scanning rate: | 2.00 C/mn |
| Amplification range: | 1.000 mV |
| Sample mass: | 25.400 mg |
| Sampling rate: | 3.68 s |
| Storage: | 1955 points |

Glass transition determination

Temperature range for Tg Determination:

| | |
|---|---|
| Beginning temperature: | 62.29 C. |
| End temperature: | 66.57 C. |
| The three Glass temperatures are: | 64.10 C. |
| | 64.55 C. |
| | 64.98 C. |
| Cp variation: | 4.56 Cal/g C. |

Integration with a linear base line

| | |
|---|---|
| Peak start: | 62.16 C. |
| Peak end: | 75.38 C. |
| Onset temperature: | 64.62 C. |
| Enthalpy: | −.18837E + 004 mJ or −.45!i·4E/003 mcal |
| | −.74161E + 002 J/g or −.17742E + 002 cal/g |
| Endothermic peak | |
| top of peak temperature: | 66.44 C. |

FIG. 4

07/08/90
DEE C109

| | |
|---|---|
| Initial temperature: | 285.2K |
| Final temperature: | 415.2K |
| Scanning rate: | 2.00 C/mn |
| Amplification range: | 1.000 mV |
| Sample mass: | 42.200 mg |
| Sampling rate: | 2.08 s |
| Storage: | 1875 points |
| Fin storage: | 1875 points in file 4 |
| Peak start: | 61.16 C. |
| Peak end: | 73.61 C. |
| Onset temperature: | 64.75 C. |
| Enthalpy: | −.30705E + 004 mJ or −.73458E/003 mcal |
| | −.72762E + 002 J/g or −.17407E + 002 cal/g |
| Endothermic peak | |
| top of peak temperature: | 66.69 C. |

Glass transition determination

Temperature range for Tg Determination:

| | |
|---|---|
| Beginning temperature: | 61.16 C. |
| End temperature: | 66.68 C. |
| The three Glass temperatures are: | 63.70 C. |
| | 64.22 C. |
| | 65.24 C. |

FIG. 5

DEE C114

| | |
|---|---|
| Initial temperature: | 285.2K |
| Final temperature: | 415.2K |
| Scanning rate: | 2.00 C/mn |
| Amplification range: | 1.00 mV |
| Sample mass: | 61.600 mg |
| Sampling rate: | 2.08 s |
| Storage: | 1875 points |

Glass transition determination

Temperature range for Tg Determination:

| | |
|---|---|
| Beginning temperature: | 57.84 C. |
| End temperature: | 67.04 C. |
| The three Glass temperatures are: | 63.60 C. |
| | 64.31 C. |
| | 65.52 C. |
| Cp variation: | 5.24 Cal/g C. |

Integration with a linear base line

| | |
|---|---|
| Peak start: | 77.00 C. |

-continued

| | |
|---|---|
| Peak end: | 64.78 C. |
| Enthalpy: | −.45478E + 004 mJ or −.10879E/004 mcal |
| | −.73828E + 002 J/g or −.17662E + 002 cal/g |
| Endothermic peak | |
| top of peak temperature: | 66.90 C. |

FIG. 6

07/08/90
DEE 109MC

| | |
|---|---|
| Initial temperature: | 285.2K |
| Final temperature: | 415.2K |
| Scanning rate: | 2.00 C/mn |
| Amplification range: | 1.000 mV |
| Sample mass: | 35.800 mg |
| Sampling rate: | 2.08 s |
| Storage: | 1875 points |
| Fin. Storage: | 1875 points in file 5 |

Integration with a linear base line

| | |
|---|---|
| Peak start: | 61.75 C. |
| Peak end: | 73.26 C. |
| Onset temperature: | 64.65 C. |
| Enthalpy: | −.26206E + 004 mJ or −.62695E/003 mcal |
| | −.73203E + 002 J/g or −.17512E + 002 cal/g |
| Endothermic peak | |
| top of peak temperature: | 66.90 C. |

Glass transition determination

Temperature range for Tg Determination:

| | |
|---|---|
| Beginning temperature: | 61.65 C. |
| End temperature: | 67.04 C. |
| The three Glass temperatures are: | 64.40 C. |
| | 64.57 C. |
| | 65.59 C. |
| Cp variation: | 7.48 Cal/g C. |

FIG. 7

Ref. 9007033

Coulter ® LS Particle size analysis A0890.S18

| | | | |
|---|---|---|---|
| Filename: | A0890.S18 | Group ID: | A0-890 |
| Sample ID: | TX 066 LOT 037 MC2 | Run number: | 6 |
| Operator: | A.P.C. SIMM | | |
| Comments: | DISPERSION: glycerol & U. SOUND COULTRONICS FRANCE | | |
| Start time: | 10:42 25 aug 1990 | | |
| Run length: | 90 seconds | | |
| Obscuration: | 6% | | |
| PIDS Obscur: | 30% | | |
| Optical model: | Fraunhofer PIDS included | | |
| PC: | Version 1.10 13:07 Fri Mar 02 1990 | | |
| Calculations from | 0.10 μm to 834.40 μm | | |
| Volume | 100.0 % | | |
| Mean | 22.49 μm | 95% Conf. limits: | 19-42-25-56 μm |
| Median | 19.72 μm | Std. Dev: | 15-67 μm |
| Mean/median Ratio | 1.341 | Variance: | 245.5 μm² |
| Mode | 29.60 μm | Coef. var: | 69.66 % |
| | | Skewness: | 7.016e-001 Right skewed |
| | | Kurtois: | −1.088e-001 Platy-kurtic |

| % | 10.00 | 25.00 | 50.00 | 75.00 | 90.00 |
|---|---|---|---|---|---|
| Size μm | 45.20 | 32.64 | 19.72 | 10.10 | 3.771 |

FIG. 8

DATA TREATMENT OF A CURVE STDRED: SCANNING MODE: INTEGRATION, CRYSTALLINITY AND GLASS TRANSITION DETERMINATIONS

11/04/90
THERAMEX A

| | |
|---|---|
| Initial temperature: | 290.2K |
| Final temperature: | 525.2K |
| Scanning rate: | 2.00 C/mn |
| Amplification range: | 10.00 mV |
| Sample mass: | 51.300 mg |
| Sampling rate: | 1.92 s |
| Storage: | 3671 points |

Glass transition determination

-continued

| Temperature range for Tg Determination: | |
|---|---|
| Beginning temperature: | 172.9 C. |
| End temperature: | 181.5 C. |
| The three Glass temperatures are: | 176.9 C. |
| | 178.7 C. |
| | 179.9 C. |
| Pente = : | −13.2346027168 |

Integration with a linear base line

| | |
|---|---|
| Peak start: | 173.9 C. |
| K1 = | 2.490 |
| S(K$_1$) = | −3.1655 |
| Peak end: | 191.1 C. |
| K2 | 2760 |
| S(K$_2$) | −3.1354 |
| Enthalpy: | −3.487E + 003 mJ or −1.626E/001 mcal or −6.797E + 001 J/g |

Endothermic peak

| | |
|---|---|
| TP = | 181.881617 |
| top of peak temperature: | 180.1 C. |

11/04/90
THERAMEX B

| | |
|---|---|
| Initial temperature: | 290.2K |
| Final temperature: | 525.2K |
| Scanning rate: | 5.00 C/mn |
| Amplification range: | 2.500 mV |
| Sample mass: | 15.600 mg |
| Sampling rate: | .80 s |
| Storage: | 3524 points |

Integration with a linear base line

| | |
|---|---|
| Peak start: | 169.6 C. |
| K1 | 2356 |
| S(K$_1$) | −2.3444 |
| Peak end: | 199.5 C. |
| K2 | 2806 |
| S(K$_2$) | −1.8524 |
| Enthalpy: | −1.052E + 003 mJ or −1.618E/001 mcal −6.748E + 001 J/g |

Endothermic peak

| | |
|---|---|
| TP = | 181.919107A6 |
| top of peak temperature: | 180.2 C. |

Glass transition determination

Temperature range for Tg Determination:

| | |
|---|---|
| Beginning temperature: | 169.5 C. |
| End temperature: | 181.5 C. |
| The three Glass temperatures are: | 176.4 C. |
| | 178.1 C. |
| | 179.5 C. |
| Pente: | −6.4818199304 |

FIG. 9

11/04/90
THERAMEX C

| | |
|---|---|
| Initial temperature: | 290.2K |
| Final temperature: | 525.2K |
| Scanning rate: | 5.00 C/mn |
| Amplification range: | 2.500 mV |
| Sample mass: | 10.500 mg |
| Sampling rate: | .80 s |
| Storage: | 3524 points |

Integration with a linear base line

| | |
|---|---|
| Peak start: | 173.6 C. |
| K1 | 2417 |
| S(K$_1$) | −1.7128 |
| Peak end: | 199.5 C. |
| K2 | 2807 |
| S(K$_2$) | −1.4299 |
| Enthalpy: | −7.215E + 002 mJ or −1.644E/001 mcal or −6.872E + 001 J/g |

Endothermic peak

| | |
|---|---|
| TP = | 180.985774333 |
| top of peak temperature: | 179.2 C. |

Glass transition determination

Temperature range for Tg Determination:

| | |
|---|---|
| Beginning temperature: | 173.5 C. |
| End temperature: | 180.5 C. |
| The three Glass temperatures are: | 177.2 C. |
| | 178.9 C. |
| | 179.4 C. |
| Pente: | −11.8392024107 |

THERAMEX D

| | |
|---|---|
| Initial temperature: | 290.2K |
| Final temperature: | 525.2K |
| Scanning rate: | 5.00 C/mn |
| Amplification range: | 2.500 mV |
| Sample mass: | 15.900 mg |
| Sampling rate: | .80 s |
| Storage: | 3524 points |

Integration with a linear base line

| | |
|---|---|
| Peak start: | 175.5 C. |
| K1 | 2446 |
| S(K$_1$) | −2.4676 |
| Peak end: | 194.5 C. |
| K2 | 2731 |
| S(K$_2$) | −2.3127 |
| Enthalpy: | −1.114E + 003 mJ or −1.677E/001 mcal or −7.011E + 001 J/g |

Endothermic peak

| | |
|---|---|
| TP | 181.252441 |
| top of peak temperature: | 179.0 C. |

Glass transition determination

Temperature range for Tg Determination:

| | |
|---|---|
| Beginning temperature: | 173.5 C. |
| End temperature: | 181.0 C. |
| The three Glass temperatures are: | 178.0 C. |
| | 179.1 C. |
| | 179.7 C. |
| Pente: | −21.4280794192 |

FIG. 11

Ref. 9007032
COULTER ® LS Particle size analysis A0889.S01

| | | | |
|---|---|---|---|
| Filename: | A0889.S01 | Group ID: | A0-889 |
| Sample ID: | TX 066 LOT 037 MC1 | Run number: | 1 |
| Operator: | A.P.C SIMM | | |
| Comments: | DISPERSION: NONIDET & U. SOUND COULTER FRANCE | | |
| Start time: | 11.55 24 aug 1990 | | |
| Run length: | 91 seconds | | |
| Obscuration: | 5% | | |
| PIDS Obscur: | 23% | | |
| Optical model: | Fraunhofer PIDS included | | |
| PC: | Version 1.10 13:07 Fri Mar 02 1990 | | |
| | Volume Statistics (Arithmetic) 10889.S01 | | |
| Calculations from | 0.10 μm to 834.40 μm | | |
| Volume | 100.0 % | | |
| Mean | 32.93 μm | 95% Conf. limits: | 29-02-26-84 μm |
| Median | 31.12 μm | Std. Dev: | 18-96 μm |
| Mean/median Ratio | 1.058 | Variance: | 396.4 μm$^2$ |
| Mode | 44.70 μm | Coef. var: | 60.61 % |
| | | Skewness: | 3.640e-001 Right skewed |
| | | Kurtois: | −5.857e-001 Platy-kurtic |
| % | 10.00 | 25.00 | 50.00 | 75.00 | 90.00 |
| Size μm | 65.21 | 47.02 | 31.12 | 17.07 | 7.810 |

FIG. 12

| Operator: | FP | Sample: | MC2 |
|---|---|---|---|
| 16 Oct. 1991 | | | 16:03 |
| Field area: | 30543.81 | Calibration: | 0.2717 mcm/pixel |
| Field 1: | | Class 2: | |
| Feat. | Area | Perimeter | Long dimsn. |
| 1 | 60.181 | 34.189 | 13.055 |
| 2 | 96.954 | 38.947 | 14.827 |
| 3 | 45.634 | 26.169 | 9.2551 |
| 4 | 69.116 | 33.109 | 12.772 |
| 5 | 58.409 | 30.959 | 12.107 |
| 6 | 53.277 | 29.411 | 10.818 |
| 7 | 37.807 | 28.331 | 12.375 |
| 8 | 49.732 | 29.488 | 11.273 |
| 9 | 59.295 | 29.303 | 10.788 |
| 10 | 48.292 | 27.650 | 9.6381 |
| 11 | 49.474 | 27.094 | 10.229 |
| 12 | 39.727 | 27.849 | 11.145 |
| 13 | 57.818 | 31.689 | 11.848 |
| 14 | 32.490 | 24.579 | 9.6381 |

-continued

| | | |
|---|---|---|
| 15 | 44.231 | 25.782 | 9.4914 |
| 16 | 29.832 | 22.428 | 7.9550 |
| 17 | 102.086 | 40.780 | 15.910 |
| 18 | 46.188 | 30.739 | 13.058 |
| 19 | 47.443 | 30.379 | 12.261 |
| 20 | 50.877 | 28.224 | 10.233 |
| Total | 1078.86 | 597.098 | 228.675 |
| Mean | 53.943 | 29.855 | 11.434 |
| St Dev. | 18.281 | 4.4267 | 1.9422 |

FIG. 13

| N.M.A. 028-028B 031-031B | | | |
|---|---|---|---|
| 028001.DT3 | 05-30-1991 | 13:50:40 | |
| Y-scale | 008 AU/FS | Sample name | tx(1-00-1) |
| Sampling time | 21 msec *4 | Paper speed | 4 mm/min |
| Sense | normal | | |
| Resolution | 3 nm | Column ultrosphere DDS 4,6 mm ID S250 mm | |
| Time range | 2.4–25 min | Packing material C18 | |
| Interval | 1 sec | Mobile phase Acetonitrile 360 | |
| Baseline | OFF | Flow rate MeOH 240 | 1,3 ml/min |
| Smoothing | 5 points | Pressure | 2.300 psi |
| Drift | .002 AU/min | Slope H$_2$O 400 | .0001 AU/min |
| Width | .001 min | Height | .0002 AU |
| Time double | 30 min | Min. area | .00002 AU*min |
| | | Minus peak | OFF |

What is claimed is:

1. A process for crystallizing a product comprising a pharmaceutically active ingredient of steroidal structure to obtain without any mechanical procedure a homogenous class of product which may be prepared beforehand comprising dissolving the product to be crystallized in a ternary mixture of a lipophilic solvent, a hydrophilic solvent and a surface active agent at a temperature close to the boiling point of the ternary mixture, allowing the ternary mixture to cool to a temperature where crystallization occurs and recovering the resulting crystals.

2. A process according to claim 1 wherein the active ingredient is an estrane derivative.

3. A process according to claim 2 wherein the estrane derivative is selected from the group consisting of estradiol, estrone, estriol, 19-nor Testosterone, the 3-mono ethers of the same, the 3, 17-diethers of these compounds and the esters of these compounds.

4. A process according to claim 1 wherein the active ingredient is an androstane derivative.

5. A process according to claim 4 wherein the derivative of androstane is selected from the group consisting of Testosterone, ethers of Testosterone, esters of Testosterone, Testosterones substituted by a halogen or a lower alkyl in position 4, 6, 7 or 16 and the 17α-ethynyl-17β-acetoxy-5α-androst-2-ene.

6. A process according to claim 1 wherein the active ingredient is a pregnane derivative.

7. A process according to claim 6 wherein the pregnane derivative is a steroidal compound selected from the group consisting of progesterone, enolic ethers of progesterone, cyclic or linear enamines of progesterone, 17α-hydroxy progesterones, esters of 17α-hydroxy progesterone, progesterones substituted by an alkyl, a trifluoromethyl or a halogen in position 1,6,7 and/or 16 and the ethers or esters thereof.

8. A process according to claim 1 wherein the active ingredient is a 19-nor pregnane derivative.

9. A process according to claim 8 wherein the derivative of 19-nor pregnane is a steroidal derivative selected from the group consisting of 17α-hydroxy-19-nor-progesterone, the ethers in position 17 of 17α-hydroxy-19-nor-progesterone, 6-methyl-17α-hydroxy-19-nor-progesterone, ethers in position 17 of 6-methyl-17α-hydroxy-19-nor-progesterone, esters in position 17 of 6-methyl-17α-hydroxy-19-nor-progesterone, 6-methyl-3,20-dioxo-17α-hydroxy-19-nor-pregna-4,6-diene and the esters in position 17 of 6-methyl-17α-hydroxy-19-nor-pregna-4,6-diene and the 17α- and 21-methyl or ethyl analogs of 6-methyl-3,20-dioxo-19-nor-pregna-4,6-diene.

10. A process according to claim 1 wherein the active ingredient is a derivative of cholestane.

11. A process according to claim 1 wherein the active ingredient is a derivative of 21-hydroxy Δ4-pregnene.

12. A process according to claim 10 wherein the 21-hydroxy Δ4-pregnenic derivative is a corticosteroid selected from the group consisting of Cortisone, Prednisone, Dexamethasone, Betamethasone, Triamcinolone, Medrol, Cortivazol, their esters in position 17, their diesters in positions 17 and 21 and their esters in position 21.

13. A process according to claim 1 wherein the lipophilic solvent is selected from the group consisting of alkanols, ketones, alkyl esters and cyclic ethers in which the hydrophilic solvent has to be miscible in an amount up to 12%.

14. A process according to claim 13 wherein the hydrophilic solvent is selected in such a manner to be miscible with the lipophilic solvent in order to insure a homogeneous solution.

15. A process according to claim 13 wherein the hydrophilic solvent is an aqueous mixture made of one or several oxygenated solvents.

16. A process according to claim 13 wherein the hydrophilic solvent is selected from the group consisting of water and/or polar solvents and/or lower alkyl esters of cycloalkylcarboxylates.

17. A process according to claim 1 wherein the surface active agent is an anionic surfactive agent.

18. A process according to claim 17 wherein the anionic surfactive agent is soluble in the lipophilic solvent or in the hydrophilic solvent and necessarily at the same time in the mixture of both solvents.

19. A process according to claim 1 wherein the anionic surface active agent is selected from the group consisting of the polyoxyethylenic esters of sorbitan and fatty acids, having at least 8 carbon atoms the polyoxyethylenic esters of stearic acid and the copolymers of ethylene oxide and propylene oxide.

20. A process according to claim 1 wherein the ternary mixture, made of a lipophilic solvent, a hydrophilic solvent and a surface active agent, is realized in one or several steps.

21. A process according to claim 1 wherein the concentration of the surface active agent in the ternary mixture lies between 0.01 and 10%.

22. A process according to claim 21 wherein the concentration in surface active agent in the ternary mixture lies between 0.05 and 5%.

23. A process according to claim 1 wherein the ternary mixture containing the active ingredient to be crystallized, is heated to a temperature as close as possible to the boiling point of the mixture of solvent in order to insure the highest possible concentration of the compound to be crystallized and to decrease the temperature of crystallisation of the said compound.

24. The microcrystallized products of the process according to claim 1.

* * * * *